US010525151B2

(12) United States Patent
Lee et al.

(10) Patent No.: US 10,525,151 B2
(45) Date of Patent: Jan. 7, 2020

(54) METHOD FOR PREPARING ORGANIC FLUORIDE-ALIPHATIC COMPOUND AND METHOD FOR PURIFYING ORGANIC FLUORIDE-ALIPHATIC COMPOUND

(71) Applicant: THE ASAN FOUNDATION, Seoul (KR)

(72) Inventors: Sang-ju Lee, Seoul (KR); Seung-jun Oh, Seoul (KR); Dae-hyuk Moon, Seoul (KR); Jin-sook Ryu, Seoul (KR); Jae-seung Kim, Seoul (KR); Jong-jin Lee, Seoul (KR)

(73) Assignee: THE ASAN FOUNDATION, Seoul (KR)

( * ) Notice: Subject to any disclaimer, the term of this patent is extended or adjusted under 35 U.S.C. 154(b) by 110 days.

(21) Appl. No.: 15/524,705

(22) PCT Filed: Nov. 6, 2015

(86) PCT No.: PCT/KR2015/011955
§ 371 (c)(1),
(2) Date: May 5, 2017

(87) PCT Pub. No.: WO2016/072801
PCT Pub. Date: May 12, 2016

(65) Prior Publication Data
US 2017/0319720 A1    Nov. 9, 2017

(30) Foreign Application Priority Data

Nov. 7, 2014  (KR) .................. 10-2014-0154592
Nov. 7, 2014  (KR) .................. 10-2014-0154593
Sep. 8, 2015  (KR) .................. 10-2015-0126731

(51) Int. Cl.
| A61K 51/04 | (2006.01) |
| A61K 51/02 | (2006.01) |
| C07C 17/38 | (2006.01) |
| C07C 17/383 | (2006.01) |
| C07C 17/389 | (2006.01) |
| C07C 19/08 | (2006.01) |
| C07C 21/18 | (2006.01) |
| C07B 59/00 | (2006.01) |

(52) U.S. Cl.
CPC .............. *A61K 51/04* (2013.01); *A61K 51/02* (2013.01); *C07B 59/00* (2013.01); *C07C 17/38* (2013.01); *C07C 17/383* (2013.01); *C07C 17/389* (2013.01); *C07C 19/08* (2013.01); *C07C 21/18* (2013.01)

(58) Field of Classification Search
None
See application file for complete search history.

(56) References Cited

U.S. PATENT DOCUMENTS

2014/0213757 A1   7/2014  Shales et al.
2015/0202332 A1*  7/2015  Hay ................... A61K 51/0406
                                                            424/1.81

FOREIGN PATENT DOCUMENTS

| KR | 10-2004-0065076 A | 7/2004 | |
| KR | 10-0789847 B1 | 12/2007 | |
| KR | 10-1009712 B1 | 1/2011 | |
| KR | 10-2012-0089417 A | 8/2012 | |
| KR | 10-2013-0087816 A | 8/2013 | |
| KR | 10-2013-0087821 A | 8/2013 | |
| WO | WO-2012032029 A1 * | 3/2012 | ......... A61K 51/0406 |
| WO | WO 2012-092110 A2 | 7/2012 | |

OTHER PUBLICATIONS

Middleton "New Fluorinating Reagents. Dialkylaminosulfur Fluorides", J. Org. Chem., vol. 40, No. 5, 1975 (Year: 1975).*
https://www.waters.com/webassets/cms/library/docs/wa20300.pdf, printed from the web May 15, 2019 (Year: 2019).*
International Search Report for PCT/KR2015/011955.
Ali Agool et al., "Effect of radiotherapy and chemotherapy on bone marrow activity: a 18F-FLT-PET study", Nuclear Medicine Communications, vol. 32 No. 1, pp. 17-22, 2011.
Nicolas Aide et al., "18F-FLT PET as a Surrogate Marker of Drug Efficacy During mTOR Inhibition by Everolimus in a Preclinical Cisplatin-Resistant Ovarian Tumor Model", The Journal of Nuclear Medicine, vol. 51, No. 10, pp. 1559-1564, Oct. 2010.
Annelies Debucquoy et al., "18F-FLT and 18F-FDG PET to measure response to radiotherapy combined with celecoxib in two colorectal xenograft models", International Journal of Radiation Biology, vol. 85, No. 9, pp. 763-771, Sep. 2009.
R. Bolton, "Radiohalogen incorporation into organic systems", Journal of Labelled Compounds and Radiopharmaceuticals, vol. 45, pp. 485-528, 2002.
Ken-ichi Nishijima et al., "Increased [18F]2-fluoro-2-deoxy-d-glucose ([18F]FDG) yield with recycled target [18O]water: factors affecting the [18F]FDG yield", Applied Radiation and Isotopes, vol. 57, pp. 43-49, 2002.

(Continued)

*Primary Examiner* — James W Rogers
(74) *Attorney, Agent, or Firm* — The PL Law Group, PLLC

(57) ABSTRACT

A method for preparing a radiopharmaceutical and, specifically, a method for preparing an organic fluoride-aliphatic compound usable as a radiopharmaceutical, a method for purifying the prepared organic fluoride-aliphatic compound, and a method for preparing a radiopharmaceutical by using a cassette comprising a backdraft preventing reaction container. A method for preparing an organic fluorinated aliphatic compound includes allowing a fluorine salt to react with a leaving group-containing aliphatic compound by using a multifunctional solvent represented by the following Chemical Formula 1 to obtain an aliphatic compound labeled with [$^{18}$F] fluoride substituting for the leaving group. The organic fluoride-aliphatic compound can be prepared and purified through even a simple process at high yield, high efficiency, and high purity, and the radiopharmaceutical can be safely prepared without damage to a synthetic apparatus.

23 Claims, 1 Drawing Sheet

(56) References Cited

OTHER PUBLICATIONS

SNM Newsline, The Journal of Nuclear Medicine vol. 32, No. 1, 15N, Jan. 1991.
Dale Schoeller, "The Shortage of 0-18 Water", Obesity Research, vol. 7, No. 5, p. 519, Sep. 1999.
Katsuhiko Ohsaki et al., "Polymer-supported Catalysts for Efficient On-column Preparation of 2-Deoxy-2-[18F]fluoro-D-glucose", Applied Radiation and Isotopes, vol. 49, No. 4, pp. 373-378, 1998.

\* cited by examiner

METHOD FOR PREPARING ORGANIC FLUORIDE-ALIPHATIC COMPOUND AND METHOD FOR PURIFYING ORGANIC FLUORIDE-ALIPHATIC COMPOUND

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/011955, filed on Nov. 6, 2015, which claims priority to the benefit of Korean Patent Application No. 10-2014-0154592 filed on Nov. 7, 2014, 10-2014-0154593 filed on Nov. 7, 2014, and 10-2015-0126731 filed on Sep. 8, 2015 in the Korean Intellectual Property Office, the entire contents of which are incorporated herein by reference.

TECHNICAL FIELD

The present disclosure relates to a method for preparing an organic fluorinated aliphatic compound and a method for purifying an organic fluorinated aliphatic compound. More particularly, the present disclosure relates to a method for preparing an organic fluorinated aliphatic compound by using a novel multifunctional solvent and a method for purifying an organic fluorinated aliphatic compound by using solid phase extraction (SPE).

In addition, the present disclosure relates to a method for preparing a radiopharmaceutical by using a cassette including a backflow-preventing reaction container.

BACKGROUND ART

Development of modern civilization leads to improvement of life quality and development of medical science leads to an increase in human life. On the contrary, there has been a gradual increase in generation of brain diseases, such as Parkinson's diseases, depressive disorder, schizophrenia and Alzheimer's disease; heart diseases caused by stress and a change in dietary life; and various cancers caused by the exposure of the human body to various harmful materials. Thus, there has been a need for developing an imaging diagnosis method capable of diagnosing such diseases in early stages.

Various imaging diagnosis methods have been commercialized. Particularly, a method directly applicable to clinic includes positron emission tomography (PET), which can image the in vivo distribution and biochemical variation process of a radiopharmaceutical by carrying out intravenous injection of an organic compound labeled with a radioactive isotope emitting positrons to the body. Therefore, it is possible to quantitatively determine a biochemical change in the body at the site of a lesion through such positron emission tomography, and thus to measure a degree of disease progress and to predict a degree of treatment [A. Agool, R. H. Slart, K. K. Thorp, A. W. Glaudemans, D. C. Cobben, L. B. Been, F. R. Burlage, P. H. Elsinga, R. A. Dierckx, E. Vellenga, J. L. Holter, Nucl. Med. Commun. 2011, 32, 14; N. Aide, K. Kinross, C. Cullinane, P. Roselt, K. Waldeck. O, Neels, D. Dorow, G. McArthur, R. J. Hicks, J. Nucl. Med. 2011, 51, 1559; A. Debucquoy, E. Devos, P. Vermaelen, W. Landuyt, S. De Weer, F. Van Den Heuvel, K. Haustermans, Int. J. Radiat. Biol. 2009, 85, 763.].

A radiopharmaceutical is a material administered to the human body after being labeled with a radioactive isotope to diagnose or treat diseases. The radioactive isotope used for such a radiopharmaceutical is unstable and is converted into a stable isotope while emitting radiation. The radiation emitted herein may be used for diagnosis or treatment of diseases. Radiation includes alpha-ray (α-ray), beta-ray (β-ray), gamma-ray (γ-ray), positron (β+-ray), or the like. Meanwhile, radioactive isotopes used for positron emission tomography include fluoride ($[^{18}F]F$), carbon ($[^{15}C]C$), nitrogen ($[^{13}N]N$), oxygen ($[^{15}O]O$), gallium ($[^{68}Ga]Ga$), or the like. Among them, $[^{18}F]$ fluoride has a size similar to that of hydrogen, forms a stable bonding with a carbon atom in an organic compound, is produced with ease and shows an adequate half-life (110 minutes), and thus is reported to be very suitable for carrying out positron emission tomography [Lasne, M. C.; Perrio, C.; Rouden, J.; Bane, L.; Roeda, D.; Dolle, F.; Crouzel, C. Contrast Agents II, Topics in Current Chemistry, Springer-Verlag, Berlin, 2002, 222, 201-258; Bolton, R. J. Labeled Compd. Radiopharm. 2002, 45 485-528].

According to a method for forming $[^{18}F]$ fluoride, a cyclotron, which is a circular collider, is used generally to irradiate positrons to $[^{18}O]H_2O$ [M. R. Kilbourn, J. T. Hood, M. J. Welch, Int. J. Appl. Radiat. Isot. 1984, 35, 599; G K. Mulholland, R. D. Hichwa, M. R. Kilbourn, J. Moskwa, J. Label. Compd. Radiopharm. 1989, 26, 140.]. In general, $[^{18}F]$ fluoride is produced in $[^{18}O]H_2O$ solution at a significantly diluted concentration. In addition, $[^{18}O]H_2O$ solution is very expensive and thus is recycled and reused [K.-I, Nishijima, Y. Kuge, E. Tsukamoto, K.-I. Seki, K. Ohkura, Y. Magata, A. Tanaka, K. Nagatsu, N. Tamaki. Appl. Radiat. Isot. 2002, 57, 43; D. Schoeller, Obes. Res. 1999, 7, 519; SNM Newsline, J. Nucl. Med. 1991, 32, 15N.].

In order to remove a small amount of metal impurities produced when recycling the above mentioned $[^{18}O]H_2O$ and forming $[^{18}F]$ fluoride and to allow use of $[^{18}F]$ fluoride alone in a labeling reaction, a method for exchanging anions with a quaternary alkylammonium salt-supported polymer cartridge (Chromafixor QMA) is used generally [D. J. Schlyer, M. Bastos, A. P. Wolf, J. Nucl. Med. 1987, 28, 764; S. A. Toorongian, G. K. Mulholland, D. M. Jewett, M. A. Bachelor, M. R. Kilbourn, Nucl. Med. Biol. 1990, 17, 273; D. M. Jewett, S. A. Toorongian, G. K. Mulholland, G. L. Watkins, M. R. Kilbourn, Appl. Radiat. Isot. 1988, 39, 1109; G. K. Mulholland, R. D. T. J. Mangner, D. M. Jewett, M. R. Kilbourn, J. Label. Compd. Radiopharm. 1989, 26, 378; K. Ohsaki, Y. Endo, S. Yamazaki, M. Tomoi, R. Iwata, Appl. Radiat. Isot. 1998, 49, 373-378.].

Reaction of $[^{18}F]$ fluoride retained in the quaternary alkylammonium salt-supported polymer cartridge uses a metal salt, such as $K_2CO_3$, or aqueous solution containing an ammonium salt, such as $TBAHCO_3$, dissolved therein. Due to the basicity of the salts used herein, side reactions, such as alcohol or alkene reactions, occur, thereby causing degradation of labeling efficiency undesirably. In addition, when HPLC is used to purify the resultant organofluoro-18 compound, overlap with a complex byproduct may occur to show low non-radioactivity [S. M. Okarvi, Eur. J. Nucl. Med. 2001, 28, 929; J. C. Walsh, K. M. Akhoon, N. Satyamurthy, J. R. Barrio, M. M. Phelps, S. S. Gambhir, T. Toyokuni, J. Label. Compds. Radiopharm. 1999, 42, 51; L. Lang, W. C. Eckelman, Appl. Radiat. Isot. 1994, 45, 1155; L. Lang, W. C. Eckelman, Appl. Radiat. Isot. 1997, 48, 169.].

In general, it is known that a nucleophilic substitution reaction is carried out in the presence of a polar aprotic solvent, such as acetonitrile ($CH_3CN$), DMF and DMSO in order to increase the reactivity of a nucleophile, i.e. fluoride. However, according to a recent report, an alcohol solvent weakens the ionic bonding between a metal cation and a fluorine anion through hydrogen bonding with a fluorine metal salt to increase the nucleophilic substitution reactivity of a fluorine salt and to reduce the basicity of the bases used for [$^{18}$F] fluoride labeling, thereby inhibiting the side reactions [D. W. Kim, D. S. Ahn, Y. H. Oh, S. Lee, H. S. Kil, S. J. Oh, S. J. Lee, J. S. Kim, J. S. Ryu, D. H. Moon, D. Y. Chi. J. Am. Chem. Soc. 2006, 128, 16394; S. J. Lee, S. J. Oh, D. Y. Chi, H. S. Kil, E. N. Kim, J. S. Ryu, D. H. Moon, Eur. J. Nucl. Med. Mol. Imaging. 2007, 34, 1406.].

The above-mentioned problem causes consumption of a precursor due to the base used for labeling. To solve the problem, it is possible to use a method for labeling an organic compound with [$^{18}$F] fluoride by using, as a reaction solvent, a tertiary alcohol capable of reducing the basicity of the base and preventing consumption of the precursor. However, in the case of t-butanol, which is an example of such tertiary alcohols having the simplest structure, it has a low boiling point of 83° C. and thus cannot increase the reaction temperature undesirably. As another example, t-amyl alcohol has an increased boiling point of about 100° C. However, t-amyl alcohol cannot be regarded as a reaction solvent having an optimized boiling point, considering the [$^{18}$F] fluoride labeling reaction temperature is 100° C. or higher.

In addition, t-amyl alcohol is not miscible with water. After the [$^{18}$F] fluoride labeling reaction, the alcohol solvent should be removed, when a hydrolysis process and a purification process using high performance liquid chromatography (HPLC) or solid phase extraction (SPE) are necessary. Thus, when the solvent is not removed completely, there is a problem in that the solvent may be mixed with impurities during a purification process.

In general, the alcohol solvent used for the reaction is removed through a drying process. However, since such a process is time-consuming, there is a problem in that the actual reaction yield is decreased due to degradation of radioactivity caused by the half-life of a radioactive isotope used for labeling when the radioactive isotope has a relatively short half-life. In addition, in this case, when the radioactive isotope evaporates along with the organic solvent, a problem of environmental pollution occurs. Further, when using t-amyl alcohol frequently by using an automatic synthesis system, a part having no resistance against t-amyl alcohol during its evaporation may be damaged, resulting in a failure in preparation of a radiopharmaceutical.

Meanwhile, in order to protect workers from radioactivity during the preparation of a radiopharmaceutical, an automatic synthesis system is used in a space, so-called a hot cell, shielded with lead, and such automatic synthesis systems may be classified into non-cassette type systems (TracerLab FXFN, GE Healthcare; Modular Lab, E&Z, or the like) and cassette type systems (TracerLab MX, GE Healthcare; FastLab, GE Healthcare; AIO module, Trasis, or the like).

In the case of a non-cassette type automatic synthesis system, it is used mainly for the purpose of research and requires washing inconveniently after its use. On the other hand, a cassette type automatic synthesis system uses a disposal cassette and requires no additional washing. In addition, when exchanging a cassette, the cassette type automatic synthesis system may be used advantageously twice or more per day. First of all, the cassette type automatic synthesis system is applied to Good Manufacturing Practice (GMP) with ease. Therefore, in the case of a radiopharmaceutical requiring frequent preparation, use of a cassette type automatic synthesis system has more advantages as compared to a non-cassette type automatic synthesis system.

However, in order to allow use of such a cassette type automatic synthesis system, conditions (type of a reaction solvent, reaction temperature, reaction time, or the like) under which a radiopharmaceutical to be obtained is prepared should be adequate for a cassette. If not, a cassette may be damaged during the preparation of a radiopharmaceutical, resulting in a failure in preparation of the radiopharmaceutical.

A reaction container (see, (A) in FIG. 2) introduced to a cassette used for a cassette type automatic synthesis system includes a reagent-supplying line 11a to recover the reactants after reaction. Generally, the reagent-supplying line is designed to reach the bottom surface of the reaction container 10a in order to increase the recovery ratio (see, (A) in FIG. 2). In addition, the bottom may be formed into a round shape or V-like shape to increase the recovery ratio. Therefore, when the temperature in the reaction container 10a is increased and the solution is vaporized so that a positive pressure is applied into the reaction container 10a, the solvent causes backflow to the reagent-supplying line 11a which reaches the bottom surface. As a result, the cassette connected to the other end of the reagent-supplying line 11a is filled with the reaction solvent during the reaction time. Herein, when the cassette is made of a material having no resistance against the reaction solvent or the reaction temperature is significantly higher than the boiling point of the reaction solvent, the cassette is damaged by the pressure applied thereto, which may lead to a failure in preparation of a radiopharmaceutical. In addition, the solution flowing back to the reagent-supplying line 11a cannot participate in the reaction, and thus the whole reagents cannot participate in the reaction, resulting in a large variation in yield. This makes it difficult to ensure stability of yield. As a result, it is not possible to obtain a radiopharmaceutical adequate for GMP.

To solve the above-mentioned problems, cassettes made of a material having resistance against various solvents have been developed mostly in foreign countries. In the case of a cassette made of such a novel material, they are too expensive to be used as a disposable item. Thus, it is not cost-efficient to use such a disposable cassette in a large amount. In another method, a pinch valve is installed in the line undergoing backflow from the reactor so that the solution may not be retained in the cassette. However, such a method cannot prevent a backflow phenomenon fundamentally but merely is a temporary means for preventing the backflowing solution from being retained in the cassette.

In addition, in the case of the reaction container 10a designed in such a manner that the reagent-supplying line 11a reaches the bottom surface of the reaction container 10a (see, (A) in FIG. 2), the reagents splatter to the whole walls of the reaction container 10a due to the supply rate of the reagents, when the reagents are supplied through the reagent-supplying line 11a. Further, during the process for preparing a radiopharmaceutical labeled with F-18, a drying step is carried out to provide F-18 with reactivity after it is eluted out of the anion exchange cartridge. Herein, when nitrogen is supplied through the same line, nitrogen is supplied into the solution filled in the reaction container 10a and the supplied nitrogen causes generation of bubbles. Therefore, drying is carried out while the reagents splatter to the whole walls of the reaction container. When the solution containing a precursor is supplied back to the reaction container 10a through the reagent-supplying line 11a after drying F-18, the precursor also splatters to the wall of the reaction container 10a. Thus, participation of the reagents dried while being deposited on the walls varies each time, resulting in a variation in yield of a radiopharmaceutical. Particularly, in the case of a radiopharmaceutical sensitive to the amount of reagents, not only a variation in yield but also frequent failures in preparation thereof occur. As a result, it is difficult to accomplish stable preparation of a radiopharmaceutical.

SUMMARY

A technical problem to be solved by the present disclosure is to provide a method for preparing an organic fluorinated aliphatic compound by using a novel multifunctional solvent. More particularly, there is provided a method for preparing an organic fluorinated aliphatic compound by using a multifunctional solvent having a functional group capable of improving the labeling efficiency with a radioactive isotope and a functional group capable of improving the purification efficiency in order to solve the above-mentioned problems of a polar aprotic solvent and polar protic solvent used for labeling with a radioactive isotope.

Another technical problem to be solved by the present disclosure is to provide a method for effectively purifying the organic fluorinated aliphatic compound by solid phase extraction (SPE) using an ion exchange SPE cartridge.

Still another technical problem to be solved by the present disclosure is to provide a method for preparing a radiopharmaceutical by using a cassette including a backflow-preventing reaction container. More particularly, there is provided a method for preparing a radiopharmaceutical by using a cassette including a backflow-preventing reaction container which allows a reagent used for the preparation of a radiopharmaceutical to be supplied to the reaction container stably in an amount intended for participation in the reaction.

Yet another technical problem to be solved by the present disclosure is to provide a method for preparing a radiopharmaceutical by using a cassette including a backflow-preventing reaction container which prevents the reaction solvent from backflowing due to vaporization or the like while labeling is carried out at high temperature so that the cassette may not be damaged and the whole reaction solvent may participate in labeling.

In one general aspect, there is provided a method for preparing an organic fluorinated aliphatic compound, which includes a step of allowing a fluorine salt to react with a leaving group-containing aliphatic compound by using a multifunctional solvent represented by the following Chemical Formula 1 to obtain an aliphatic compound labeled with [$^{18}$F] fluoride substituting for the leaving group:

[Chemical Formula 1]

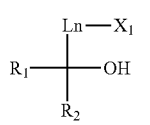

wherein each of $R_1$ and $R_2$ independently represents H, a C1-C10 alkyl group or the same functional group as $X_1$; Ln represents a C1-C10 alkyl group or is a polyethylene glycol represented by $CH_2(OCH_2CH_2)_n$ wherein n is an integer of 1-10; $X_1$ represents any one polar group selected from an alkoxy group ($OR_3$), nitrile group (CN) and halide; and $R_3$ represents a C1-C10 alkyl group).

Preferably, Ln may be a C1-C3 alkyl group or polyethylene glycol represented by $CH_2(OCH_2CH_2)n$ wherein n is an integer of 1-3.

The alkoxy group ($OR_3$) may include any one selected from methoxy, ethoxy, propoxy, isopropoxy and t-butoxy.

The halide may include any one selected from chloride (Cl), bromide (Br) and iodide (I).

Preferably, each of $R_1$ and $R_2$ may include a methyl group or ethyl group.

The multifunctional solvent represented by Chemical Formula 1 may include any one selected from the group consisting of 1-methoxy-2-methyl-2-propanol, 1-ethoxy-2-methyl-2-propanol, 1-propoxy-2-methyl-2-propanol, 1-isopropoxy-2-methyl-2-propanol, 1-t-butoxy-2-methyl-2-propanol, 1-nitrile-2-methyl-2-propanol, 1-chloro-2-metyl-2-propanol, 1-bromo-2-methyl-2-propanol, 1-iodo-2-methyl-2-propanol, 1-(2-methoxyethoxy)-2-methyl-2-propanol and 3-(methoxymethyl)-3-pentanol.

The fluorine salt used as a source of [$^{18}$F] fluoride may include a compound containing fluorine-18.

The aliphatic compound may be one having an alkyl halide group or alkyl sulfonate group, wherein the halide group or sulfonate group is a leaving group.

The aliphatic group may be one having an alkyl halide group or alkyl sulfonate group, wherein the halide group or sulfonate group is a primary leaving group or a secondary leaving group.

The aliphatic group may be one represented by N—(CH$_2$)$_n$—X$_2$ or O—(CH$_2$)$_n$—X$_2$ (wherein X$_2$ is a leaving group and n is an integer of 1-10).

X$_2$ may be a halide group or sulfonate group.

The halide group may be any one selected from the group consisting of Cl, Br and I.

The sulfonate group may be —SO$_3$R$_{12}$ (wherein R$_{12}$ is any one selected from a C1-C12 alkyl, halo C1-C12 alkyl, phenyl, C1-C4 alkylphenyl, halophenyl, C1-C4 alkoxy and nitrophenyl).

The method may further include a step of purifying the [$^{18}$F] fluoride-labeled aliphatic compound by using at least one ion exchange SPE cartridge.

The ion exchange SPE cartridge may include any one selected from a cation exchange SPE cartridge and an anion exchange SPE cartridge.

The ion exchange SPE cartridge may include a solid support including a polymer containing a phenyl group and C1-C20 hydrocarbon or silica.

The cation exchange SPE cartridge may include any one selected from an SCX (silica-based strong cation exchange) SPE cartridge, MCX (polymer-based strong cation exchange) SPE cartridge and WCX (polymer-based weak cation exchange) SPE cartridge.

The anion exchange SPE cartridge may include any one selected from an SAX (silica-based strong anion exchange) SPE cartridge, MAX (polymer-based strong anion exchange) SPE cartridge and WAX (polymer-based weak anion exchange) SPE cartridge.

In another aspect, the method for purifying an organic fluorinated aliphatic compound includes a step of purifying the organic fluorinated aliphatic compound through solid phase extraction (SPE) carried out by using an ion exchange SPE cartridge represented by the following Chemical Formula 2:

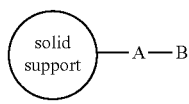

[Chemical Formula 2]

wherein the solid support is a polymer containing a phenyl group and C1-C20 hydrocarbon or silica;

A may be null when the solid support is a polymer or represents a phenyl or C1-C20 hydrocarbon group when the solid support is silica; and B may be an organic cation or an organic anion and the organic cation is (i)

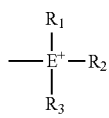

(wherein E is nitrogen or phosphorus, and $R_1$, $R_2$ and $R_3$ may be the same or different from one another, and each represents C1-C20 hydrocarbon group), (ii) an Ar having at least one nitrogen atom

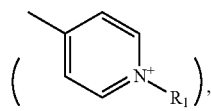

or (iii) a C2-C20 heteroaromatic cation having at least two nitrogen atoms, nitrogen and oxygen, or nitrogen and sulfur, and having a substituent of a C1-20 hydrocarbon group at the position of one nitrogen atom

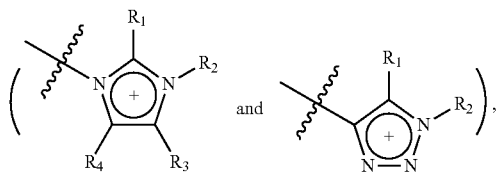

and the organic anion is sulfonic acid (—$SO^{3-}$) or carboxylic acid (—$COO^-$).

The purification may be carried out by purifying the organic fluorinated aliphatic compound by using an ion exchange SPE cartridge of Chemical Formula 2 wherein B is an organic cation in combination with an ion exchange cartridge of Chemical Formula 2 wherein B is an organic anion.

The organic fluorinated aliphatic compound may be [$^{18}$F] fluoropropyl carbomethoxytropane.

In still another aspect, there is provided a method for purifying an organic fluorinated aliphatic compound which includes a step of purifying the organic fluorinated aliphatic compound through solid phase extraction (SPE) carried out by using at least one ion exchange SPE cartridge, wherein the organic fluorinated aliphatic compound is [$^{18}$F] fluoropropyl carbomethoxytropane.

The ion exchange SPE cartridge may include any one selected from a cation exchange SPE cartridge and an anion exchange SPE cartridge.

The ion exchange SPE cartridge may include a solid support including a polymer containing a phenyl group and C1-C20 hydrocarbon or silica.

The cation exchange SPE cartridge may include any one selected from an SCX (silica-based strong cation exchange) SPE cartridge, MCX (polymer-based strong cation exchange) SPE cartridge and WCX (polymer-based weak cation exchange) SPE cartridge.

The anion exchange SPE cartridge may include any one selected from an SAX (silica-based strong anion exchange) SPE cartridge, MAX (polymer-based strong anion exchange) SPE cartridge and WAX (polymer-based weak anion exchange) SPE cartridge.

In still another aspect, there is provided a method for preparing a radiopharmaceutical by using a cassette including a backflow-preventing reaction container, the method including the steps of: eluting [$^{18}$F] fluoride through the backflow-preventing reaction container; drying the eluent in the backflow-preventing reaction container; and supplying a radiopharmaceutical precursor and a reaction solvent to the backflow-preventing reaction container and allowing the dried [$^{18}$F] fluoride to react with the radiopharmaceutical precursor in the presence of the reaction solvent, wherein the backflow-preventing reaction container includes a first line for supplying reagents for preparing the radiopharmaceutical and a second line for providing a vacuum state, the end point of the first line is present at least at a position higher than the surface of the reagents for preparing the radiopharmaceutical supplied to the backflow-preventing reaction container.

The end point may be spaced apart from the surface of reagents by at most 5 cm.

The cassette including a backflow-preventing container may include a manifold type cassette.

The reaction solvent may include any one selected from an aprotic solvent, protic solvent and a multifunctional solvent.

The aprotic solvent may include any one selected from acetonitrile, dimethyl formamide and dimethyl sulfoxide.

The protic solvent may include any one selected from the group consisting of primary alcohols including methanol, ethanol, n-propanol, n-butanol, n-amyl alcohol, n-hexyl alcohol, n-heptanol and n-octanol, secondary alcohols including isopropanol, isobutanol, isoamyl alcohol and 3-pentanol, and tertiary alcohols including t-butanol, t-amyl alcohol, 2,3-dimethyl-2-butanol, 2-(trifluoromethyl)-2-propanol, 3-methyl-3-pentaol, 3-ethyl-3-pentanol, 2-methyl-2-pentaol, 2,3-dimethyl-3-pentanol, 2,4-dimethyl-2-pentanol, 2-methyl-2-hexanol, 2-cyclopropyl-2-propanol, 2-cyclopropyl-2-butanol, 2-cyclopropyl-3-methyl-2-butanol, 1-methylcyclopentaol, 1-ethylcyclopentaol, 1-propylcyclopentaol, 1-methylcyclohexanol, 1-ethylcyclohexanol and 1-methylcycloheptanol.

The multifunctional solvent may include a compound represented by Chemical Formula 1:

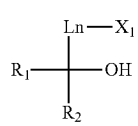

[Chemical Formula 1]

wherein each of $R_1$ and $R_2$ independently represents H, a C1-C10 alkyl group or the same functional group as $X_1$;

Ln represents a C1-C10 alkyl group or is a polyethylene glycol represented by $CH_2(OCH_2CH_2)_n$ wherein n is an integer of 1-10; and $X_1$ represents any one polar group selected from an alkoxy group ($OR_3$), nitrile group (CN) and halide).

$R_3$ represents a C1-C10 alkyl group, and the halide may include any one selected from chloride (Cl), bromide (Br) and iodide (I).

The multifunctional solvent represented by Chemical Formula 1 may include any one selected from the group consisting of 1-methoxy-2-methyl-2-propanol, 1-ethoxy-2-methyl-2-propanol, 1-propoxy-2-methyl-2-propanol, 1-iso-propoxy-2-methyl-2-propanol, 1-t-butoxy-2-methyl-2-propanol, 1-nitrile-2-methyl-2-propanol, 1-chloro-2-metyl-2-propanol, 1-bromo-2-methyl-2-propanol, and 1-iodo-2-methyl-2-propanol.

According to the embodiments of the present disclosure, there is provided a method for preparing an organic fluorinated aliphatic compound by using a multifunctional solvent containing a functional group capable of improving the labeling efficiency with a radio isotope and a functional group capable of improving purification efficiency. The functional group capable of improving the labeling efficiency with a radio isotope inhibits the side reactions caused by the side effect of a base, and thus allows high yield in labeling with a radio isotope. The functional group capable of improving purification efficiency increases the polarity of a reaction solvent so that it may be mixed well with water, and avoids a need for an additional process of removing the reaction solvent alone. Thus, it is possible to reduce the time required for preparing a radiopharmaceutical and to simplify the process for preparing a radiopharmaceutical. In addition, it is possible to carry out purification with high efficiency. Further, the linker by which multiple functional groups are connected causes an increase in boiling point, so that a reaction temperature optimized for labeling with fluorine-18 may be set, thereby allowing optimization of the preparation of a radiopharmaceutical.

In addition, according to the embodiments of the present disclosure, there is provided a method for purifying an organic fluorinated aliphatic compound through solid phase extraction (SPE) carried out in an ion exchange SPE cartridge. Therefore, it is possible to remove substantially all the impurities remaining after the preparation of an organic fluorinated aliphatic compound effectively.

In addition, according to the embodiments of the present disclosure, there is provided a method for preparing a radiopharmaceutical by using a cassette including a backflow-preventing reaction container which allows reagents for the preparation of the radiopharmaceutical to be supplied to the reaction container stably in an amount intended to participate in the reaction without loss and thus provides high yield.

Further, according to the embodiments of the present disclosure, there is provided a method for preparing a radiopharmaceutical by using a cassette including a backflow-preventing reaction container which prevents a reaction solvent from backflowing due to vaporization while labeling is carried out at high temperature so that the cassette may not be damaged and all the reaction solvent supplied to the reaction container may participate in labeling.

Therefore, it is possible for reagents for the preparation of a radiopharmaceutical to participate in labeling stably and totally in an amount supplied to the reaction container. Thus, it is possible to obtain a radiopharmaceutical with a small deviation in synthesis yield without any failure. This allows preparation of a radiopharmaceutical suitable for Good Manufacturing Practice (GMP) to be introduced in the future. In addition, since no backflow of a reaction solvent occurs, it is not required for the cassette to be resistant against the reaction solvent. Thus, it is possible to provide high cost-efficiency in preparing a radiopharmaceutical.

DETAILED DESCRIPTION

Figure 1:
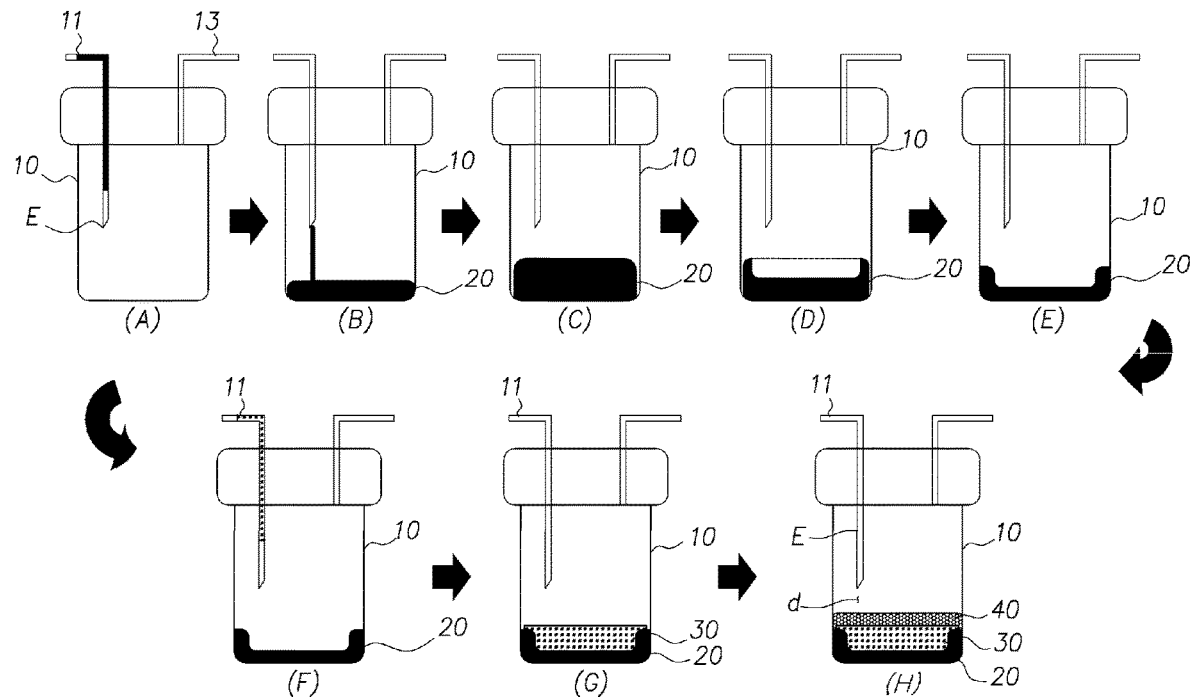
FIG. 1 is a schematic view illustrating a process for preparing a radiopharmaceutical by using a cassette including a backflow-preventing reaction container according to an embodiment.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. In the description, details of well-known features and techniques may be omitted. In the drawings, like reference numerals denote like elements.

First, the method for preparing an organic fluorinated aliphatic compound by using a novel multifunctional solvent and the method for purifying the organic fluorinated aliphatic compound by using SPE will be explained in detail.

In one aspect, there is provided a method for preparing an organic fluorinated aliphatic compound, which includes a step of allowing a fluorine salt to react with a leaving group-containing aliphatic compound by using a multifunctional solvent represented by the following Chemical Formula 1 to obtain an aliphatic compound labeled with [$^{18}$F] fluoride substituting for the leaving group:

[Chemical Formula 1]

wherein each of $R_1$ and $R_2$ independently represents H, a C1-C10 alkyl group or the same functional group as $X_1$; Ln represents a C1-C10 alkyl group or is a polyethylene glycol represented by $CH_2(OCH_2CH_2)_n$ wherein n is an integer of 1-10; $X_1$ represents any one polar group selected from an alkoxy group ($OR_3$), nitrile group (CN) and halide; and $R_3$ represents a C1-C10 alkyl group).

The fluorine salt is used as a source of [$^{18}$F] fluoride and is a compound containing fluorine-18. The fluorine salt may be selected from: alkali metal fluorides containing an alkali metal selected from the group consisting of lithium, sodium, potassium, rubidium and cesium; alkaline earth metal fluorides containing an alkaline earth metal selected from the group consisting of magnesium, calcium, strontium and barium; and ammonium fluorides. More preferably, the fluorine salt is potassium fluoride or ammonium fluoride. The potassium-containing alkali metal fluoride or tetraalkylammonium fluoride is preferably adsorbed on any one support selected from Celite, molecular sieves, alumina and silica gel. Preferably, the ammonium fluoride may be selected from the group consisting of: quaternary ammonium fluorides including tetrabutylammonium fluoride and benzyltrimethylammonium fluoride; tertiary ammonium fluorides including triethylammonium fluoride and tributylammonium fluoride; secondary ammonium fluorides including dibutylammonium fluoride and dihexylammonium fluoride; and primary ammonium fluorides including butylammonium fluoride and hexylammonium fluoride. More preferably, the ammonium fluoride may be tetrabutylammonium fluoride.

According to the present disclosure, the aliphatic compound having a leaving group is an aliphatic compound having an alkyl halide group or alkyl sulfonate group, wherein the halide group or sulfonate group functions as a leaving group. Otherwise, the halide group or sulfonate group may function as a primary leaving group or secondary leaving group. The halide group includes any one selected from the group consisting of Cl, Br and I, and the sulfonate group is $-SO_3R_{12}$ (wherein $R_{12}$ is any one selected from the group consisting of a C1-C12 alkyl, halo C1-C12 alkyl, phenyl, C1-C4 alkylphenyl, halophenyl, C1-C4 alkoxyphenyl and nitrophenyl). Particular examples of the alkylsulfonate group (wherein $R_{12}$ is a C1-C12 alkyl or halo C1-C12 alkyl) may include methane sulfonate, ethane sulfonate, isopropane sulfonate, chloromethane sulfonate, trifluoromethane sulfoante or chloroethane sulfonate. Particular examples of the aryl sulfonate group (wherein $R_{12}$ is phenyl, a C1-C4 alkylphenyl, halophenyl, C1-C4 alkoxyphenyl or nitrophenyl) may include methylphenyl sulfonate, ethylphenyl sulfonate, chlorophenyl sulfonate, bromophenyl sulfonate, methoxyphenyl sulfonate or nitrophenylsulfonyl.

According to another embodiment, the aliphatic compound having a leaving group may include an aliphatic compound having $N-(N-(CH_2)_n-X_2$ or $O-(CH_2)_n-X_2$ (wherein $X_2$ is a leaving group and n is an integer of 1-10).

Herein, $X_2$ includes a halide group or sulfonate group, the halide group includes any one selected from the group consisting of Cl, Br and I, and the sulfonate group is $-SO_3R_2$ (wherein $R_{12}$ is any one selected from the group consisting of a C1-C12 alkyl, halo C1-C12 alkyl, phenyl, C1-C4 alkylphenyl, halophenyl, C1-C4 alkoxyphenyl and nitrophenyl). Particular examples of the alkylsulfonate group (wherein $R_{12}$ is a C1-C12 alkyl or halo C1-C12 alkyl) may include methane sulfonate, ethane sulfonate, isopropane sulfonate, chloromethane sulfonate, trifluoromethane sulfoante or chloroethane sulfonate. Particular examples of the aryl sulfonate group (wherein $R_{12}$ is phenyl, a C1-C4 alkylphenyl, halophenyl, C1-C4 alkoxyphenyl or nitrophenyl) may include methylphenyl sulfonate, ethylphenyl sulfonate, chlorophenyl sulfonate, bromophenyl sulfonate, methoxyphenyl sulfonate or nitrophenylsulfonyl.

For example, particular examples of the aliphatic compound having a leaving group may include the following compounds: 1-phenyl-4-(3-tosylpropyl)-phenylpiperazine

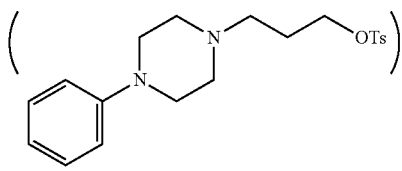

which is an organic compound having OTs as a primary leaving group, 2-(3-methanesulfonyloxypropoxy)naphthalene

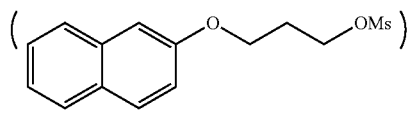

which is an organic compound having OMs as a primary leaving group, 2-(2-methanesulfonyloxypropoxy)naphthalene

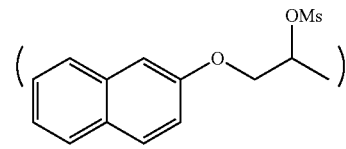

which is an organic compound having OMs as a secondary leaving group, (3-toluenesulfonyloxypropyl)-2β-carbomethoxy-3β-(4-iodophenyl)tropane which is an organic compound having OTs as a primary leaving group, (3-methanesulfonyloxypropyl)-2β-carbomethoxy-3-β-(4-iodophenyl)tropane which is an organic compound having OMs as a primary leaving group, 3-(2-nitroimidazol-1-yl)-2-O-tetrahydropyranyl-1-O-toluenesulfonyl propanediol which is an organic compound having OTs as a secondary leaving group, 5'-O-DMTr-2'-deoxy-3'-O-nosyl-b-D-threo-pentofuranoxy)-3-N-BOC-thymine which is an organic compound having ONs has a secondary leaving group, mannose triflate (1,3,4,6-tetra-O-acetyl-2-O-trifluoro-methanesulfonyl-beta-D-mannopyranose) having OTf as a secondary leaving group, (E)-4-chlorobut-2-enyl-2β-carbomethoxy-3-β-(4-iodophenyl)tropane which is an organic compound having Cl as a primary leaving group, or the like.

The organic fluorinated aliphatic compound obtained by the method for preparing an organic fluorinated aliphatic compound according to the present disclosure may also include a radiopharmaceutical. The radiopharmaceutical may include at least one selected from the following compounds:

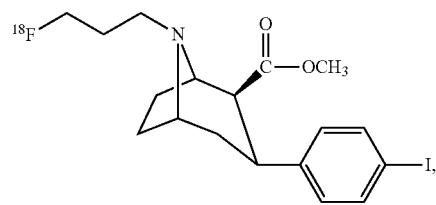

[$^{18}$F] fluoropropylcarbomethoxytropane

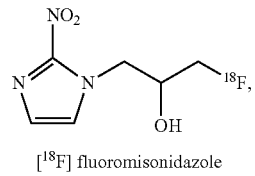

[$^{18}$F] fluoromisonidazole

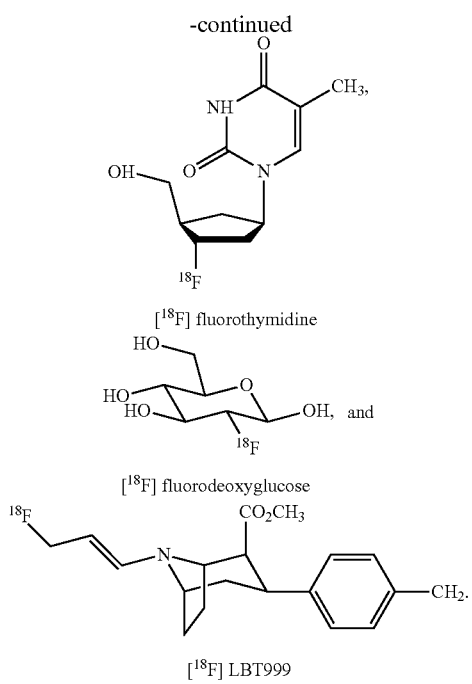

[$^{18}$F] fluorothymidine

[$^{18}$F] fluorodeoxyglucose

[$^{18}$F] LBT999

The multifunctional solvent according to an embodiment includes an alcohol group (alcohol group in Chemical Formula 1) as a functional group capable of improving the labeling efficiency with a radio isotope, a functional group capable of improving purification efficiency and a linker (Ln in Chemical Formula 1) capable of setting an optimized reaction temperature.

When labeling is carried out with [$^{18}$F] fluoride through nucleophilic substitution, a predetermined amount of base should be used and typical examples of the base include potassium carbonate or potassium hydrogen carbonate. Such bases cause a side reaction with the precursor, resulting in consumption of the precursor and degradation of the labeling efficiency with [$^{18}$F] fluoride. However, the alcohol group contained in the multifunctional solvent according to an embodiment inhibits such a side reaction with the precursor caused by the base and preserves the amount of precursor, and thus allows preparation of a radiopharmaceutical with high yield.

In addition, since $X_1$ group ($X_1$ group in Chemical Formula 1) contained in the multifunctional solvent according to an embodiment increases the polarity, the multifunctional solvent has increased solubility to water and thus may be applied to various purification methods, such as simple purification methods using a solid phase extraction (SPE) cartridge and HPLC purification methods, thereby allowing preparation of a radiopharmaceutical with high purity. According to the related art, a reaction solvent having poor solubility to water requires a drying step for removing the reaction solvent. However, the multifunctional solvent avoids such a need for a drying step, thereby reducing the reaction time.

In addition, the linker (Ln in Chemical Formula 1) contained in the multifunctional solvent according to an embodiment increases the boiling point and allows setting of an optimized reaction temperature, thereby allowing preparation of a radiopharmaceutical with high yield.

In addition, the method for preparing an organic fluorinated aliphatic compound according to an embodiment may further include a step of purifying the resultant [$^{18}$F] fluoride-labeled aliphatic compound by using at least one ion exchange SPE cartridge.

As described above, when preparing an organic fluorinated aliphatic compound by using the multifunctional solvent according to an embodiment, the resultant organic fluorinated aliphatic compound may be purified both through HPLC and SPE. However, in the case of HPLC, it may cause loss of radioactivity during purification as compared to SPE and may produce decomposition products caused by radioactivity in the case of mass production. This is problematic particularly when preparing [$^{18}$F] fluoropropylcarbomethoxytropane. In the case of the radioactive decomposition products, they have a retention time similar to that of [$^{18}$F] fluoropropylcarbomethoxytropane and cause low radiochemical purity. In addition, in the case of HPLC purification, the output may be varied with a degree of skill of a worker or researcher, which makes it difficult to produce a radiopharmaceutical stably with high quality. To solve the above problems, it is possible to carry out purification by using a reverse phase SPE cartridge currently used for formulation widely. However, when using a reverse phase SPE cartridge, despite higher radiochemical purity as compared to HPLC, it is difficult to purify impurities (intermediate compounds that remain after fluorination from the precursors used for preparation of [$^{18}$F] fluoropropylcarbomethoxytropane and undergo a change in chemical structure while not participating in fluorination) having a polarity similar to that of [$^{18}$F] fluoropropylcarbomethoxytropane. In other words, even though such impurities have a different proportion from the resultant [$^{18}$F] fluoropropylcarbomethoxytropane, they show substantially the same oleophilicity as [$^{18}$F] fluoropropylcarbomethoxytropane. Thus, it was found through the following examples that such precursor-based organic impurities may not be removed substantially when using a reverse phase SPE cartridge.

However, when using the ion exchange SPE purification method according to an embodiment, it is possible to purify [$^{18}$F] fluoropropylcarbomethoxytropane from organic impurities having similar polarity to that of [$^{18}$F] fluoropropylcarbomethoxytropane with high efficiency.

The ion exchange SPE purification method according to an embodiment uses an ion exchange SPE cartridge which may include any one selected from a cation exchange SPE cartridge and an anion exchange SPE cartridge. The ion exchange SPE cartridge may include a solid support including a polymer containing a phenyl group and C1-C20 hydrocarbon or silica. Herein, the cation exchange SPE cartridge may include any one selected from an SCX (silica-based strong cation exchange) SPE cartridge, MCX (polymer-based strong cation exchange) SPE cartridge and WCX (polymer-based weak cation exchange) SPE cartridge, and the anion exchange SPE cartridge may include any one selected from an SAX (silica-based strong anion exchange) SPE cartridge, MAX (polymer-based strong anion exchange) SPE cartridge and WAX (polymer-based weak anion exchange) SPE cartridge.

According to another embodiment, the ion exchange SPE cartridge includes an ion exchange SPE cartridge represented by the following Chemical Formula 2:

[Chemical Formula 2]

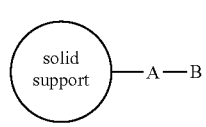

wherein the solid support is a polymer containing a phenyl group and C1-C20 hydrocarbon or silica;

A may be null when the solid support is a polymer or represents a phenyl or C1-C20 hydrocarbon group when the solid support is silica; and B may be an organic cation or an organic anion and the organic cation is (i)

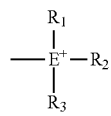

(wherein E is nitrogen or phosphorus, and $R_1$, $R_2$ and $R_3$ may be the same or different from one another, and each represents C1-C20 hydrocarbon group), (ii) an Ar having at least one nitrogen atom

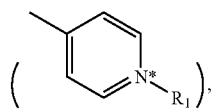

or (iii) a C2-C20 heteroaromatic cation having at least two nitrogen atoms, nitrogen and oxygen, or nitrogen and sulfur, and having a substituent of a C1-20 hydrocarbon group at the position of one nitrogen atom

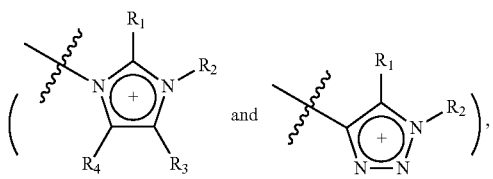

and the organic anion is sulfonic acid ($-SO^{3-}$) or carboxylic acid ($-COO^-$).

As described above, according to the present disclosure, it is possible to obtain an organic fluorinated aliphatic compound with high yield, high efficiency and high yield through the organic fluorination of an aliphatic compound having a leaving group by using a multifunctional reaction solvent. In addition, the multifunctional reaction solvent according to the present disclosure has high affinity with water and allows purification of an organic fluorinated aliphatic compound without a need for an additional solvent drying step. Further, although the organic fluorinated aliphatic compound according to the present disclosure may be purified by both HPLC and SPE, it is possible to improve even the efficiency of removing impurities remaining after the fluorination when purification is carried out by using an ion exchange SPE purification method.

Hereinafter, the present disclosure will be explained in more detail with reference to the following examples. The following examples are for illustrative purposes only and not intended to limit the scope of the present disclosure. It will be understood by those skilled in the art that various changes in form and details may be made thereto without departing from the scope of this disclosure as defined by the appended claims. Therefore, it is intended that the scope of the present disclosure includes all embodiments falling within the spirit and scope of the appended claims.

Example 1. Use of 1-Methoxy-2-Methyl-2-Propanol as Reaction Solvent

Example 1-1. Organic Fluorination of Aliphatic Compound Having OTs as Primary Leaving Group To a quaternary ammonium salt support (Chromafix or QMA), [$^{18}$F] fluoride is adsorbed by passing [$^{18}$F] fluoride therethrough to carry out ion exchange and the [$^{18}$F] fluoride adsorbed to the quaternary ammonium salt support is eluted with a mixed KOMs solution having a controlled pH to a reaction container. After the elution, the eluent is removed completely by using azeotropic distillation while nitrogen gas is introduced at 100° C.

To the reaction container, 0.1 mL of acetonitrile containing 1-phenyl-4-(3-tosylpropyl)-phenylpiperazine dissolved therein and 1.0 mL of 1-methoxy-2-methyl-2-propanol as a multifunctional reaction solvent according to the present disclosure are introduced. Then, reaction is carried out at 120° C. to obtain 1-(3-[$^{18}$F] fluoropropyl)-4-phenylpiperazine.

The labeling efficiency is determined by radioactive thin film chromatography. After the reaction, the product is diluted without drying and purified by using a solid phase extraction method. After the purification, high performance liquid chromatography is carried out to determine purity.

Example 1-2. Organic Fluorination of Aliphatic Compound Having OMs as Primary or Secondary Leaving Group The same method as Example 1-1 is used, except that 0.1 mL of acetonitrile containing each of 2-(3-methanesulfonyloxypropoxy)naphthalene (aliphatic compound having OMs as a primary leaving group) and 2-(2-methanesulfonyloxypropoxy)naphthalene (aliphatic compound having OMs as a secondary leaving group) dissolved therein, and 1.0 mL of 1-methoxy-2-methyl-2-propanol as a multifunctional reaction solvent according to the present disclosure are introduced to the reaction container. Then, reaction is carried out at 120° C. to obtain 2-(3-[$^{18}$F] fluoropropoxy)naphthalene or 2-(2-[$^{18}$F] fluoropropoxy)naphthalene.

The labeling efficiency is determined by radioactive thin film chromatography. After the reaction, the product is diluted without drying and purified by using a solid phase extraction method. After the purification, high performance liquid chromatography is carried out to determine purity.

Comparative Example 1. Use of Acetonitrile as Reaction Solvent

Comparative Example 1-1. Organic Fluorination of Aliphatic Compound Having OTs as Primary Leaving Group The same materials and method as Example 1-1 are used, except that acetonitrile is used as a reaction solvent to obtain 1-(3-[$^{18}$F] fluoropropyl)-4-phenylpiperazine.

Comparative Example 1-2. Organic Fluorination of Aliphatic Compound Having OMs as Primary or Secondary Leaving Group The same materials and method as Example 1-2 are used, except that acetonitrile is used as a reaction solvent to obtain 2-(3-[$^{18}$F] fluoropropoxy)naphthalene or 2-(2-[$^{18}$F] fluoropropoxy)naphthalene.

Comparative Example 2. Use of t-Amyl Alcohol as Reaction Solvent

Comparative Example 1-1. Organic Fluorination of Aliphatic Compound Having OTs as Primary Leaving Group The same materials and method as Example 1-1 are used, except that t-amyl alcohol is used as a reaction solvent to obtain 1-(3-[$^{18}$F] fluoropropyl)-4-phenylpiperazine.

Comparative Example 1-2. Organic Fluorination of Aliphatic Compound Having OMs as Primary or Secondary Leaving Group The same materials and method as Example 1-2 are used, except that t-amyl alcohol is used as a reaction solvent to obtain 2-(3-[$^{18}$F] fluoropropoxy)naphthalene or 2-(2-[$^{18}$F] fluoropropoxy)naphthalene.

The results are shown in the following Table 1.

TABLE 1

|  | Organofluoro-18 compound | Reaction solvent | Labeling efficiency | Yield | Radio-chemical purity |
|---|---|---|---|---|---|
| Ex. 1-1 | 1-(3-[$^{18}$F] fluoropropyl)-4-phenylpiperazine | 1-mexhoxy-2-methyl-2-propanol | 89.3% | 71.4% | 100% |
| Ex. 1-2 | 2-(3-[$^{18}$F]fluoropropoxy)naphthalene | | 94.7% | 61.5% | 100% |
|  | 2-(2-[$^{18}$F]fluoropropoxy)naphthalene | | 95.1% | 63.4% | 100% |
| Comp. Ex. 1-1 | 1-(3-[$^{18}$F]fluoropropyl)-4-phenylpiperazine | Acetonitrile | 9.1% | 6.2% | 100% |
| Comp. Ex. 1-2 | 2-(3-[$^{18}$F]fluoropropoxy)naphthalene | | 56.5% | 31.1% | 100% |
|  | 2-(2-[$^{18}$F]fluoropropoxy)naphthalene | | 43.7% | 20.4% | 100% |
| Comp. Ex. 2-1 | 1-(3-[$^{18}$F]fluoropropyl)-4-phenylpiperazine | t-amyl alcohol | 52.4% | 12.4% | 100% |
| Comp. Ex. 2-2 | 2-(3-[$^{18}$F]fluoropropoxy)naphthalene | | 96.5% | 13.7% | 100% |
|  | 2-(2-[$^{18}$F]fluoropropoxy)naphthalene | | 93.7% | 10.4% | 100% |

As can be seen from Table 1, when an organic fluorinated aliphatic compound is prepared by using the multifunctional solvent, 1-methoxy-2-methyl-2-propanol, according to the present disclosure, the labeling efficiency is at least about 90% and the yield is a least 61%, which demonstrates preparation of an organic fluorinated aliphatic compound with high yield, high purity and high efficiency. On the contrary, when using the conventional reaction solvent, t-amyl alcohol (Comparative Example 2), the labeling efficiency of an organic fluorinated aliphatic compound in the case of an O-alkyl aliphatic compound having OMs as a leaving group is at least 90% but the yield is merely 10%, which suggests that an organic fluorinated aliphatic compound cannot be prepared efficiently. The labeling efficiency of an organic fluorinated aliphatic compound in the case of an N-alkyl aliphatic compound having OTs as a leaving group is as low as 52.4% and the yield is as low as 12.4%. In addition, when using the conventional reaction solvent, acetonitrile (Comparative Example 1), the labeling efficiency of an organic fluorinated compound in the case of an N-alkyl aliphatic compound having OTs as a leaving group is significantly low (9.1%) and the yield is also significantly low (6.2%). In addition, the labeling efficiency of an organic fluorinated aliphatic compound in the case of an N-alkyl aliphatic compound having OMs as a leaving group is 56.5% or 43.7%, which is not sufficiently high, and the yield in this case is significantly low (31.1% or 20.4%), which demonstrates that an organic fluorinated aliphatic compound cannot be prepared efficiently.

Example 2. Use of 1-Chloro-2-Methyl-2-Propanol as Reaction Solvent

Example 2-1. Organic Fluorination of Aliphatic Compound Having OTs as Primary Leaving Group To a quaternary ammonium salt support (Chromafix or QMA), [$^{18}$F] fluoride is adsorbed by passing [$^{18}$F] fluoride therethrough to carry out ion exchange and the [$^{18}$F] fluoride adsorbed to the quaternary ammonium salt support is eluted with a mixed KOMs solution having a controlled pH to a reaction container. After the elution, the eluent is removed completely by using azeotropic distillation while nitrogen gas is introduced at 100° C.

To the reaction container, 0.1 mL of acetonitrile containing 1-phenyl-4-(3-tosylpropyl)-phenylpiperazine dissolved therein and 1.0 mL of 1-chloro-2-methyl-2-propanol as a multifunctional reaction solvent according to the present disclosure are introduced. Then, reaction is carried out at 120° C. to obtain 1-(3-[$^{18}$F] fluoropropyl)-4-phenylpiperazine.

The labeling efficiency is determined by radioactive thin film chromatography. After the reaction, the product is diluted without drying and purified by using a solid phase extraction method. After the purification, high performance liquid chromatography is carried out to determine purity.

Example 2-2. Organic Fluorination of Aliphatic Compound Having OMs as Primary or Secondary Leaving Group To a quaternary ammonium salt support (Chromafix or QMA), [$^{18}$F] fluoride is adsorbed by passing [$^{18}$F] fluoride therethrough to carry out ion exchange and the [$^{18}$F] fluoride adsorbed to the quaternary ammonium salt support is eluted with a mixed KOMs solution having a controlled pH to a reaction container. After the elution, the eluent is removed completely by using azeotropic distillation while nitrogen gas is introduced at 100° C.

To the reaction container, 0.1 mL of acetonitrile containing each of 2-(3-methanesulfonyloxypropoxy)naphthalene (aliphatic compound having OMs as a primary leaving group) and 2-(2-methanesulfonyloxypropoxy)naphthalene (aliphatic compound having OMs as a secondary leaving group) dissolved therein, and 1.0 mL of 1-chloro-2-methyl-2-propanol as a multifunctional reaction solvent according to the present disclosure are introduced. Then, reaction is carried out at 120° C. to obtain 2-(3-[$^{18}$F] fluoropropoxy)naphthalene or 2-(2-[$^{18}$F] fluoropropoxy)naphthalene.

The labeling efficiency is determined by radioactive thin film chromatography. After the reaction, the product is diluted without drying and purified by using a solid phase extraction method. After the purification, high performance liquid chromatography is carried out to determine purity.

TABLE 2

| Organofluoro-18 compound | Reaction solvent | Labeling efficiency | Yield | Radio-chemical purity |
|---|---|---|---|---|
| Ex. 2-1 1-(3-[$^{18}$F] flruoropropyl)-4-phenylpiperazine | 1-chloro-2-methyl-2-propanol | 58.2% | 42.3% | 100% |
| Ex. 2-2 2-(3-[$^{18}$F]fluoropropoxy)naphthalene | | 87.1% | 51.9% | 100% |
| 2-(2-[$^{18}$F]fluoropropoxy)naphthalene | | 85.4% | 53.1% | 100% |

As shown in Table 2, Example 2 uses 1-chloro-2-methyl-2-propanol as a multifunctional solvent according to the present disclosure to obtain an organic fluorinated aliphatic compound. In the case of Example 2-1, the labeling efficiency and the yield are 58.2% and 42.3%, respectively, which are approximately 6-7 times higher as compared to the conventional reaction solvent (acetonitrile according to Comparative Example 1-2 in Table 1). In addition, the yield is approximately 3 times higher than the yield of t-amyl alcohol according to Comparative Example 2-2 in Table 1.

In the case of Example 2-2, the labeling efficiency is 87.1% or 85.4% and the yield is 51.9% or 53.1%, which are approximately 2-3 times higher as compared to the conventional reaction solvent (acetonitrile according to Comparative Example 1-2 in Table 1). In addition, the yield is approximately 5 times higher than the yield of t-amyl alcohol according to Comparative Example 2-2 in Table 1.

Example 3. Use of 1-Nitrile-2-Methyl-2-Propanol as Reaction Solvent

Example 3-1. Organic Fluorination of Aliphatic Compound Having OTs as Primary Leaving Group The same materials and method as Example 2-1 are used to carry out organic fluorination of an aliphatic compound having OTs as a leaving group, except that 1-nitrile-2-methyl-2-propanol is used as a reaction solvent to obtain an organic fluorinated aliphatic compound, 1-(3-[$^{18}$F] fluoropropyl)-4-phenylpiperazine.

Example 3-2. Organic Fluorination of Aliphatic Compound Having OMs as Primary or Secondary Leaving Group The same materials and method as Example 2-2 are used to carry out organic fluorination of an aliphatic compound having OMs as a leaving group, except that 1-nitrile-2-methyl-2-propanol is used as a reaction solvent to obtain an organic fluorinated aliphatic compound, 2-(3-[$^{18}$F] fluoropropoxy)naphthalene or 2-(2-[$^{18}$F] fluoropropoxy)naphthalene.

As shown in Table 3, Example 3 uses 1-nitrile-2-methyl-2-propanol as a multifunctional solvent according to the present disclosure to obtain an organic fluorinated aliphatic compound. In the case of Example 3-1, the labeling efficiency and the yield are 42.8% and 30.2%, respectively, which are approximately 5 times higher as compared to the conventional reaction solvent (acetonitrile according to Comparative Example 1-2 in Table 1). In addition, the yield is approximately 2 times higher than the yield of t-amyl alcohol according to Comparative Example 2-2 in Table 1.

In the case of Example 3-2, the labeling efficiency is 81.3% or 83.8% and the yield is 49.4% or 50.3%, which are approximately 2-3 times higher as compared to the conventional reaction solvent (acetonitrile according to Comparative Example 1-2 in Table 1). In addition, the yield is approximately 4-5 times higher than the yield of t-amyl alcohol according to Comparative Example 2-2 in Table 1.

Example 4. Use of 3-(Methoxymethyl)-3-Pentanol as Reaction Solvent

Example 4-1. Organic Fluorination of Aliphatic Compound Having OTs as Primary Leaving Group The same materials and method as Example 2-1 are used to carry out organic fluorination of an aliphatic compound having OTs as a leaving group, except that 3-(methoxymethyl)-3-pentanol is used as a reaction solvent to obtain an organic fluorinated aliphatic compound, 1-(3-[$^{18}$F] fluoropropyl)-4-phenylpiperazine.

Example 4-2. Organic Fluorination of Aliphatic Compound Having OMs as Primary or Secondary Leaving Group The same materials and method as Example 2-2 are used to carry out organic fluorination of an aliphatic compound having OMs as a leaving group, except that 3-(methoxymethyl)-3-pentanol is used as a reaction solvent to obtain an organic fluorinated aliphatic compound, 2-(3-[$^{18}$F] fluoropropoxy)naphthalene or 2-(2-[$^{18}$F] fluoropropoxy)naphthalene.

TABLE 3

| Organofluoro-18 compound | Reaction solvent | Labeling efficiency | Yield | Radio-chemical purity |
|---|---|---|---|---|
| Ex. 3-1 1-(3-[$^{18}$F] flruoropropyl)-4-phenylpiperazine | 1-nitrile-2-methyl-2-propanol | 42.8% | 30.2% | 100% |
| Ex. 3-2 2-(3-[$^{18}$F]fluoropropoxy)naphthalene | | 81.3% | 49.4% | 100% |
| 2-(2-[$^{18}$F]fluoropropoxy)naphthalene | | 83.8% | 50.3% | 100% |

TABLE 4

| | Organofluoro-18 compound | Reaction solvent | Labeling efficiency | Yield | Radio-chemical purity |
|---|---|---|---|---|---|
| Ex. 4-1 | 1-(3-[$^{18}$F] flruoropropyl)-4-phenylpiperazine | 3-(methoxymethyl)-3-pentaol | 64.7% | 43.8% | 100% |
| Ex. 4-2 | 2-(3-[$^{18}$F]fluoropropoxy)naphthalene | | 84.3% | 54.9% | 100% |
| | 2-(2-[$^{18}$F]fluoropropoxy)naphthalene | | 83.4% | 51.7% | 100% |

As shown in Table 4, Example 4 uses 2-(methoxymethyl)-3-pentaol as a multifunctional solvent according to the present disclosure to obtain an organic fluorinated compound. In the case of Example 4-1, the labeling efficiency and the yield are 64.7% and 43.8%, respectively, which are approximately 7 times higher as compared to the conventional reaction solvent (acetonitrile according to Comparative Example 1-2 in Table 1). In addition, the yield is approximately 4 times higher than the yield of t-amyl alcohol according to Comparative Example 2-2 in Table 1.

In the case of Example 4-2, the labeling efficiency is 84.3% or 83.4% and the yield is 54.9% or 51.7%, both of which are higher as compared to Comparative Example 1-2 (using acetonitrile) and Comparative Example 2-2 (using t-amyl alcohol).

Example 5. Use of 1-(2-Methoxyethoxy)-2-Methyl-2-Propanol as Reaction Solvent

Example 5-1. Organic Fluorination of Aliphatic Compound Having OTs as Primary Leaving Group The same materials and method as Example 2-1 are used to carry out organic fluorination of an aliphatic compound having OTs as a leaving group, except that 1-(methoxyethoxy)-2-methyl-2-propanol is used as a reaction solvent to obtain an organic fluorinated aliphatic compound, 1-(3-[$^{18}$F] fluoropropyl)-4-phenylpiperazine.

Example 5-2. Organic Fluorination of Aliphatic Compound Having OMs as Primary or Secondary Leaving Group The same materials and method as Example 2-2 are used to carry out organic fluorination of an aliphatic compound having OMs as a leaving group, except that 1-(methoxyethoxy)-2-methyl-2-propanol is used as a reaction solvent to obtain an organic fluorinated aliphatic compound, 2-(3-[$^{18}$F] fluoropropoxy)naphthalene or 2-(2-[$^{18}$F] fluoropropoxy)naphthalene.

As shown in Table 5, Example 5 uses 1-(methoxyethoxy)-2-methyl-2-propanol as a multifunctional solvent according to the present disclosure to obtain an organic fluorinated aliphatic compound. In the case of Example 5-1, the labeling efficiency and the yield are 58.7% and 47.0%, respectively, which are approximately 8 times higher as compared to the conventional reaction solvent (acetonitrile according to Comparative Example 1-2 in Table 1). In addition, the yield is approximately 4 times higher than the yield of t-amyl alcohol according to Comparative Example 2-2 in Table 1.

In the case of Example 5-2, the labeling efficiency is 85.3% or 81.8% and the yield is 52.1% or 50.3%, both of which are higher as compared to Comparative Example 1-2 (using acetonitrile) and Comparative Example 2-2 (using t-amyl alcohol).

Example 6. Use of 1-Ethoxy-2-Methyl-2-Propanol as Reaction Solvent

Example 6-1. Organic Fluorination of Aliphatic Compound Having OTs as Primary Leaving Group The same materials and method as Example 2-1 are used to carry out organic fluorination of an aliphatic compound having OTs as a leaving group, except that 1-ethoxy-2-methyl-2-propanol is used as a reaction solvent to obtain an organic fluorinated aliphatic compound, 1-(3-[$^{18}$F] fluoropropyl)-4-phenylpiperazine.

Example 6-2. Organic Fluorination of Aliphatic Compound Having OMs as Primary or Secondary Leaving Group The same materials and method as Example 2-2 are used to carry out organic fluorination of an aliphatic compound having OMs as a leaving group, except that 1-ethoxy-2-methyl-2-propanol is used as a reaction solvent to obtain an organic fluorinated aliphatic compound, 2-(3-[$^{18}$F] fluoropropoxy)naphthalene or 2-(2-[$^{18}$F] fluoropropoxy)naphthalene.

TABLE 5

| | Organofluoro-18 compound | Reaction solvent | Labeling efficiency | Yield | Radio-chemical purity |
|---|---|---|---|---|---|
| Ex. 5-1 | 1-(3-[$^{18}$F] flruoropropyl)-4-phenylpiperazine | 1-(2-methoxyethoxy)-2-methyl-2-propanol | 58.7% | 47.0% | 100% |
| Ex. 5-2 | 2-(3-[$^{18}$F]fluoropropoxy)naphthalene | | 85.3% | 52.1% | 100% |
| | 2-(2-[$^{18}$F]fluoropropoxy)naphthalene | | 81.8% | 50.3% | 100% |

TABLE 6

| | Organofluoro-18 compound | Reaction solvent | Labeling efficiency | Yield | Radio-chemical purity |
|---|---|---|---|---|---|
| Ex. 6-1 | 1-(3-[$^{18}$F] flruoropropyl)-4-phenylpiperazine | 1-ethoxy-2-methyl-2-propanol | 50.1% | 39.8% | 100% |
| Ex. 6-2 | 2-(3-[$^{18}$F]fluoropropoxy)naphthalene | | 87.3% | 55.2% | 100% |
| | 2-(2-[$^{18}$F]fluoropropoxy)naphthalene | | 80.1% | 53.2% | 100% |

As shown in Table 6, Example 6 uses 1-ethoxy-2-methyl-2-propanol as a multifunctional solvent according to the present disclosure to obtain an organic fluorinated aliphatic compound. In the case of Example 6-1, the labeling efficiency and the yield are 50.1% and 39.8%, respectively, which are approximately 6 times higher as compared to the conventional reaction solvent (acetonitrile according to Comparative Example 1-2 in Table 1). In addition, the yield is approximately 3 times higher than the yield of t-amyl alcohol according to Comparative Example 2-2 in Table 1.

In the case of Example 6-2, the labeling efficiency is 87.3% or 80.1% and the yield is 55.2% or 53.2%, both of which are higher as compared to Comparative Example 1-2 (using acetonitrile) and Comparative Example 2-2 (using t-amyl alcohol).

Example 7. Preparation of [$^{18}$F] Fluoropropylcarbomethoxytropane

Example 7-1. Use of Aliphatic Compound Having OTs as Primary Leaving Group as Precursor To a quaternary ammonium salt support (Chromafix or QMA), [$^{18}$F] fluoride is adsorbed by passing [$^{18}$F] fluoride therethrough to carry out ion exchange and the [$^{18}$F] fluoride adsorbed to the quaternary ammonium salt support is eluted with a mixed KOMs solution having a controlled pH to a reaction container. After the elution, the eluent is removed completely by using azeotropic distillation while nitrogen gas is introduced at 100° C.

To the reaction container, 0.1 mL of acetonitrile containing (3-toluenesulfonyloxypropyl)-2β-carbomethoxy-3-β-(4-iodophenyl)tropane dissolved therein as a precursor and 1.0 mL of 1-methoxy-2-methyl-2-propanol as a multifunctional reaction solvent according to the present disclosure are introduced. Then, reaction is carried out at 120° C. to obtain 1-(3-[$^{18}$F] fluoropropylcarbomethoxytropane.

The labeling efficiency is determined by radioactive thin film chromatography. After the reaction, the product is diluted without drying and purified by using a solid phase extraction method. After the purification, high performance liquid chromatography is carried out to determine purity.

Example 7-2. Use of Aliphatic Compound Having OMs as Primary Leaving Group as Precursor The same method as Example 3 is used, except that (3-methanesulfonyloxypropyl)-2β-carbomethoxy-3-β-(4-iodophenyl)tropane (aliphatic compound having OMs as a leaving group) is used as a precursor to obtain [$^{18}$F] fluoropropylcarbomethoxytropane.

Comparative Example 4. Use of Acetonitrile as Reaction Solvent Comparative Example 4-1

The same materials and method as Example 7-1 are used, except that acetonitrile is used as a reaction solvent to obtain [$^{18}$F] fluoropropylcarbomethoxytropane.

Comparative Example 4-2

The same materials and method as Example 7-2 are used, except that acetonitrile is used as a reaction solvent to obtain [$^{18}$F] fluoropropylcarbomethoxytropane.

Comparative Example 5. Use of t-Amyl Alcohol as Reaction Solvent

Comparative Example 5-1

The same materials and method as Example 7-1 are used, except that t-amyl alcohol is used as a reaction solvent to obtain [$^{18}$F] fluoropropylcarbomethoxytropane.

Comparative Example 5-2

The same materials and method as Example 7-2 are used, except that t-amyl alcohol is used as a reaction solvent to obtain [$^{18}$F] fluoropropylcarbomethoxytropane.

The results are shown in the following Table 7.

TABLE 7

| | Precursor | Reaction solvent | Total synthesis time | Labeling efficiency | Yield | Radiochemical purity |
|---|---|---|---|---|---|---|
| Ex. 7-1 | -OTs | 1-methoxy-2-methyl-2-propanol | 25 min. | 92.7% | 74.2% | 100% |
| Ex. 7-2 | -OMs | | 25 min. | 77.4% | 65.7% | 100% |
| Comp. Ex. 4-1 | -OTs | Acetonitrile | 25 min. | 12.7% | 5.4% | 100% |
| Comp. Ex. 4-2 | -OMs | | 25 min. | 6.1% | 6.7% | 100% |
| Comp. Ex. 5-1 | -OTs | t-amyl alcohol | 25 min. | 45.2% | 2.9% | 87% |
| Comp. Ex. 5-2 | -OMs | | 25 min. | 41.9% | 3.1% | 82% |

As can be seen from the above results, when using the conventional reaction solvent, acetonitrile (Comparative Examples 4-1 and 4-2), the yield is as low as about 5-7% and the labeling efficiency is also as low as about 6-12%. When using the conventional reaction solvent, t-amyl alcohol (Comparative Examples 5-1 and 5-2), the labeling efficiency is about 40% or more but the yield is significantly low (2-3%). Thus, it can be seen that the conventional reaction solvents are not suitable for the preparation of an organic fluorinated aliphatic compound. On the contrary, Examples 7-1 and Examples 7-2 use 1-methyl-2-methyl-2-propanol as a multifunctional solvent according to the present disclosure, and provide a yield of 74.2% and 65.7%, respectively, which is significantly higher as compared to Comparative Examples. In addition, Examples 7-1 and 7-2 provide a labeling efficiency of 92.7% and 77.4%, respectively, which is significantly higher as compared to Comparative Examples and show a purity of 100%. Therefore, it can be seen that when using the multifunctional solvent according to the present disclosure, an organic fluorinated aliphatic compound can be obtained with high efficiency, high purity and high yield.

Example 8. Preparation of [$^{18}$F] LBT 999

In this example, an aliphatic compound having Cl as a primary leaving group is used as a precursor to obtain [$^{18}$F] LBT 999.

To a quaternary ammonium salt support (Chromafix or QMA), [$^{18}$F] fluoride is adsorbed by passing [$^{18}$F] fluoride therethrough to carry out ion exchange and the [$^{18}$F] fluoride adsorbed to the quaternary ammonium salt support is eluted with a mixed KOMs solution having a controlled pH to a reaction container. After the elution, the eluent is removed completely by using azeotropic distillation while nitrogen gas is introduced at 100° C.

To the reaction container, 0.1 mL of acetonitrile containing (E)-4-chlorobut-2-enyl-2β-carbomethoxy-3-β-(4-iodophenyl)tropane, which is an aliphatic compound having Cl as a primary leaving group, dissolved therein as a precursor and 1.0 mL of 1-methoxy-2-methyl-2-propanol as a multifunctional reaction solvent according to the present disclosure are introduced. Then, reaction is carried out at 120° C. to obtain [$^{18}$F] LBT 999.

The labeling efficiency is determined by radioactive thin film chromatography. After the reaction, the product is diluted without drying and purified by using a solid phase extraction method. After the purification, high performance liquid chromatography is carried out to determine purity. The results are shown in the following Table 8.

Example 9. Preparation of [$^{18}$F] Fluoromisonidazole

In this example, an aliphatic compound having OTs as a secondary leaving group is used as a precursor to obtain [$^{18}$F] fluoromisonidazole.

To a quaternary ammonium salt support (Chromafix or QMA), [$^{18}$F] fluoride is adsorbed by passing [$^{18}$F] fluoride therethrough to carry out ion exchange and the [$^{18}$F] fluoride adsorbed to the quaternary ammonium salt support is eluted with a mixed KOMs solution having a controlled pH to a reaction container. After the elution, the eluent is removed completely by using azeotropic distillation while nitrogen gas is introduced at 100° C.

To the reaction container, 0.1 mL of acetonitrile containing 3-(2-nitroimidazol-1-yl)-2-O-tetrahydropyranyl-1-O-toluenesulfonylpropanediol, which is an aliphatic compound having OTs as a secondary leaving group, dissolved therein as a precursor and 1.0 mL of 1-methoxy-2-methyl-2-propanol as a multifunctional reaction solvent according to the present disclosure are introduced. Then, reaction is carried out at 120° C. to carry out labeling with [$^{18}$F] fluoride and the labeling efficiency is determined by radioactive thin film chromatography. After the reaction, 1M hydrochloric acid is introduced and hydrolysis is carried out at 100° C. for 5 minutes and 2M sodium hydroxide is introduced to carry out neutralization. Then, the product is diluted with water and purified by using a solid phase extraction method. After the purification, high performance liquid chromatography is carried out to determine purity. The results are shown in the following Table 8.

Example 10. Preparation of [$^{18}$F] Fluorothymidine

In this example, an aliphatic compound having ONs as a secondary leaving group is used as a precursor to obtain [$^{18}$F] fluorothymidine.

To a quaternary ammonium salt support (Chromafix or QMA), [$^{18}$F] fluoride is adsorbed by passing [$^{18}$F] fluoride therethrough to carry out ion exchange and the [$^{18}$F] fluoride adsorbed to the quaternary ammonium salt support is eluted with a mixed KOMs solution having a controlled pH to a reaction container. After the elution, the eluent is removed completely by using azeotropic distillation while nitrogen gas is introduced at 100° C.

To the reaction container, 0.1 mL of acetonitrile containing 5'-O-DMTr-2'-deoxy-3'-O-nosyl-b-D-threo-pentofuranosyl-3-N-BOC-thymine, which is an aliphatic compound having ONs as a secondary leaving group, dissolved therein as a precursor and 1.0 mL of 1-methoxy-2-methyl-2-propanol as a multifunctional reaction solvent according to the present disclosure are introduced. Then, reaction is carried out at 120° C. to carry out labeling with [$^{18}$F] fluoride and the labeling efficiency is determined by radioactive thin film chromatography. After the reaction, 1M hydrochloric acid is introduced and hydrolysis is carried out at 100° C. for 5 minutes and 2M sodium hydroxide is introduced to carry out neutralization. Then, the product is diluted with water and purified by using a solid phase extraction method. After the purification, high performance liquid chromatography is carried out to determine purity. The results are shown in the following Table 8.

Example 11. Preparation of [$^{18}$F] Fluorodeoxyglucose

In this example, an aliphatic compound having OTf as a secondary leaving group is used as a precursor to obtain [$^{18}$F] fluorodeoxyglucose.

To a quaternary ammonium salt support (Chromafix or QMA), [$^{18}$F] fluoride is adsorbed by passing [$^{18}$F] fluoride therethrough to carry out ion exchange and the [$^{18}$F] fluoride adsorbed to the quaternary ammonium salt support is eluted with a mixed KOMs solution having a controlled pH to a reaction container. After the elution, the eluent is removed completely by using azeotropic distillation while nitrogen gas is introduced at 100° C.

To the reaction container, 0.1 mL of acetonitrile containing mannose triflate (1,3,4,6-tetra-O-acetyl-2-O-trifluoromethanesulfonyl-beta-D-manno pyranose), which is an aliphatic compound having OTf as a secondary leaving group, dissolved therein as a precursor and 1.0 mL of 1-methoxy-2-methyl-2-propanol as a multifunctional reaction solvent according to the present disclosure are introduced. Then, reaction is carried out at 120° C. to carry out labeling with [$^{18}$F] fluoride and the labeling efficiency is determined by radioactive thin film chromatography. After the reaction, 1M hydrochloric acid is introduced and hydrolysis is carried out at 100° C. for 5 minutes and 2M sodium hydroxide is introduced to carry out neutralization. Then, the product is diluted with water and purified by using a solid phase extraction method. After the purification, high performance liquid chromatography is carried out to determine purity.

Examples 8-11 show preparation of various radiopharmaceuticals using 1-methoxy-2-methyl-2-propanol as a multifunctional solvent according to the present disclosure, and the labeling efficiency, purification method, purification time and yield of each example are also shown in the following Table 8.

TABLE 8

| | Organofluoro-18 compound | Labeling efficiency | Purification method | Purification time | Yield | Radiochemical purity |
|---|---|---|---|---|---|---|
| Ex. 8 | [$^{18}$F] LBT 999 | 87.4% | SPE | 5 Min. | 57.4% | 100% |
| Ex. 9 | [$^{18}$F] fluoromisonidazole | 97.4% | | | 65.1% | 100% |
| Ex. 10 | [$^{18}$F] fluorothymidine | 95.7% | | | 63.4% | 100% |
| Ex. 11 | [$^{18}$F] fluorodeoxyglucose | 93.7% | | | 66.4% | 100% |

[$^{18}$F] LBT 99 according to Example 8, [$^{18}$F] fluoromisonidazole according to Example 9, [$^{18}$F] fluorothymidine according to Example 10 and [$^{18}$F] fluorodeoxyglucose according to Example 11 are radiopharmaceuticals used clinically in Korea and other foreign countries now and are prepared by using 1-methoxy-2-methyl-2-propanol as a multifunctional solvent according to the present disclosure. As shown in Table 8, all the radiopharmaceuticals have a purity of 100% and the radiopharmaceuticals show a significantly high labeling efficiency of 97.4%, 95.7%, 90.5% and 93.7% and a high yield of 65.1%, 63.4%, 61.7% and 66.4%. Thus, as can be seen from the above results, it is possible to obtain radiopharmaceuticals by using the multifunctional solvent according to the present disclosure with high yield, high purity and high efficiency.

Example 12. Purification of [$^{18}$F] Fluoropropylcarbomethoxytropane

Example 12-1. Purification Using Solid Phase Extraction (SPE)

To purify (Example 12-1-1) [$^{18}$F] fluoropropylcarbomethoxytropane obtained from Example 7-1 and to purify (Example 12-1-2) [$^{18}$F] fluoropropylcarbomethoxytropane obtained from Example 7-2, the resultant products are diluted with water without drying and purified by using a reverse phase solid phase extraction (SPE) method, when the synthesis of [$^{18}$F] fluoropropylcarbomethoxytropane is completed by adding a precursor and reaction solvent according to Examples 7-1 and 7-2. After the purification, high performance liquid chromatography is carried out to determine the purity of the products.

Example 12-2. Purification Using High Performance Liquid Chromatography (HPLC)

To purify (Example 12-2-1) [$^{18}$F] fluoropropylcarbomethoxytropane obtained from Example 7-1 and to purify (Example 12-2-2) [$^{18}$F] fluoropropylcarbomethoxytropane obtained from Example 7-2, the resultant products are diluted with water without drying and purified by using high performance liquid chromatography, when the synthesis of [$^{18}$F] fluoropropylcarbomethoxytropane is completed by adding a precursor and reaction solvent according to Examples 7-1 and 7-2. After the purification, high performance liquid chromatography is carried out to determine the purity of the products.

The results of Example 12 are shown in the following Table 9.

Comparative Example 6. Purification of Fluoropropylcarbomethoxytropane

Comparative Example 6-1. Purification Using Solid Phase Extraction (SPE)

To purify (Comparative Example 6-1-1) [$^{18}$F] fluoropropylcarbomethoxytropane obtained from Comparative Example 4-1 and to purify (Example 6-1-2) [$^{18}$F] fluoropropylcarbomethoxytropane obtained from Comparative Example 4-2, the resultant products are diluted with water without drying and purified by using a reverse phase solid phase extraction (SPE) method, when the synthesis of [$^{18}$F] fluoropropylcarbomethoxytropane is completed by adding a precursor and reaction solvent according to Comparative Examples 4-1 and 4-2. After the purification, high performance liquid chromatography is carried out to determine the purity of the products.

Comparative Example 6-2. Purification Using High Performance Liquid Chromatography (HPLC)

To purify (Comparative Example 6-2-1) [$^{18}$F] fluoropropylcarbomethoxytropane obtained from Comparative Example 4-1 and to purify (Comparative Example 6-2-2) [$^{18}$F] fluoropropylcarbomethoxytropane obtained from Comparative Example 4-2, the resultant products are diluted with water without drying and purified by using high performance liquid chromatography, when the synthesis of [$^{18}$F] fluoropropylcarbomethoxytropane is completed by adding a precursor and reaction solvent according to Comparative Examples 4-1 and 4-2. After the purification, high performance liquid chromatography is carried out to determine the purity of the products.

The results of Comparative Example 6 are shown in the following Table 9.

Comparative Example 7. Purification of [$^{18}$F] Fluoropropylcarbomethoxytropane

Comparative Example 7-1. Purification Using Solid Phase Extraction (SPE)

To purify (Comparative Example 7-1-1) [$^{18}$F] fluoropropylcarbomethoxytropane obtained from Comparative Example 5-1 and to purify (Example 7-1-2) [$^{18}$F] fluoropropylcarbomethoxytropane obtained from Comparative Example 5-2, the resultant products are diluted with water without drying and purified by using a reverse phase solid phase extraction (SPE) method, when the synthesis of [$^{18}$F] fluoropropylcarbomethoxytropane is completed by adding a precursor and reaction solvent according to Comparative Examples 5-1 and 5-2. After the purification, high performance liquid chromatography is carried out to determine the purity of the products.

Comparative Example 7-2. Purification Using High Performance Liquid Chromatography (HPLC)

To purify (Comparative Example 7-2-1) [$^{18}$F] fluoropropylcarbomethoxytropane obtained from Comparative Example 5-1 and to purify (Comparative Example 7-2-2) [$^{18}$F] fluoropropylcarbomethoxytropane obtained from Comparative Example 5-2, the resultant products are diluted with water without drying and purified by using high performance liquid chromatography, when the synthesis [$^{18}$F] fluoropropylcarbomethoxytropane is completed by adding a precursor and reaction solvent according to Comparative Examples 5-1 and 5-2. After the purification, high performance liquid chromatography is carried out to determine the purity of the products.

The results of Comparative Example 7 are shown in the following Table 9.

Comparative Example 8. Purification of [$^{18}$F] Fluoropropylcarbomethoxytropane

Comparative Example 8-1. Purification Using Solid Phase Extraction (SPE)

The same materials and methods as Comparative Examples 7-1-1 and 7-1-2 are used, except that [$^{18}$F] fluoropropylcarbomethoxytropane is subjected to drying after the preparation thereof and then purified. Then, the yield and radiochemical purity are determined.

Comparative Example 8-2. Purification Using High Performance Liquid Chromatography (HPLC)

The same materials and methods as Comparative Examples 7-2-1 and 7-2-2 are used, except that [$^{18}$F] fluoropropylcarbomethoxytropane is subjected to drying after the preparation thereof and then purified. Then, the yield and radiochemical purity are determined.

The results of Comparative Example 8 are shown in the following Table 9.

TABLE 9

| | Precursor | Total synthesis time | Labeling efficiency | Purification method | Purification time | Yield | Radiochemical purity |
|---|---|---|---|---|---|---|---|
| Ex. 12-1-1 | -OTs | 25 min. | 92.7% | SPE | 15 min. | 74.2% | 100% |
| Ex. 12-1-2 | -OMs | | 77.4% | | | 65.7% | 100% |
| Ex. 12-2-1 | -OTs | 25 min. | 83.2% | HPLC | 30 min. | 44.7% | 100% |
| Ex. 12-2-2 | -OMs | | 71.5% | | | 40.1% | 100% |
| Comp. Ex. 6-1-1 | -OTs | 25 min. | 12.7% | SPE | 15 min. | 6.7% | 100% |
| Comp. Ex. 6-1-2 | -OMs | | 6.1% | | | 5.4% | 100% |
| Comp. Ex. 6-2-1 | -OTs | 25 min. | 8.9% | HPLC | 30 min. | 2.1% | 100% |
| Comp. Ex. 6-2-2 | -OMs | | 11.8% | | | 2.4% | 100% |
| Comp. Ex. 7-1-1 | -OTs | 25 min. | 45.2% | SPE | 15 min. | 2.9% | 87% |
| Comp. Ex. 7-1-2 | -OMs | | 41.9% | | | 3.1% | 82% |
| Comp. Ex. 7-2-1 | -OTs | 25 min. | 42.7% | HPLC | 30 min. | 8.7% | 100% |
| Comp. Ex. 7-2-2 | -OMs | | 47.4% | | | 7.5% | 100% |
| Comp. Ex. 8-1-1 | -OTs | 40 min. | 58.7% | SPE | 15 min. | 36.4% | 100% |
| Comp. Ex. 8-1-2 | -OMs | | 53.9% | | | 34.1% | 100% |
| Comp. Ex. 8-2-1 | -OTs | 40 min. | 60.4% | HPLC | 30 min. | 21.7% | 100% |
| Comp. Ex. 8-2-2 | -OMs | | 47.1% | | | 18.5% | 100% |

As shown in Table 9, when the multifunctional solvent according to the present disclosure is used to prepare [$^{18}$F] fluoropropylcarbomethoxytropane, the labeling efficiency, yield and radiochemical purity are significantly higher as compared to the conventional reaction solvents, acetonitrile (Comparative Example 6) and t-amyl alcohol (Comparative Example 7), even though the subsequent purification step is carried out by using SPE (Example 12-1) and HPLC (Example 12-2).

However, the multifunctional solvent according to the present disclosure provides a higher yield when purification is carried out by using SPE (Example 12-1) rather than HPLC (Example 12-2).

Meanwhile, in the case of Example 12, Comparative Example 6 and Comparative Example 7, no drying step is used when purification is carried out and [$^{18}$F] fluoropropylcarbomethoxytropane is purified through each purification method. In Comparative Example 8, a drying step is used and then [$^{18}$F] fluoropropylcarbomethoxytropane is purified through each purification method. As a result, Comparative Example 8 shows a slightly increased synthesis time due to the drying step as compared to the other examples using no drying step. Due to the drying step, the total synthesis time is increased by about 15 minutes. The yield is reduced by about 50% or less as compared to Example 12, due to the loss of radioactivity during the drying step.

Example 13. Reverse Phase Purification Method of [$^{18}$F] Fluoropropylcarbomethoxytropane When using the reverse phase SPE method used in Example 12-1 to carry out purification, it is possible to obtain [$^{18}$F] fluoropropylcarbomethoxytropane with high radiochemical purity, high labeling efficiency and high yield. However, after the synthesis, impurities having polarity similar to that of [$^{18}$F] fluoropropylcarbomethoxytropane are present. Thus, a reverse phase purification method is used to determine whether such impurities can be purified or not.

Example 13-1. Purification Using Reverse Phase High Performance Liquid Chromatography (HPLC)

The same materials and method as Example 7-2 are used, except that 8 mL of 70% methanol is used to carry out dilution after the synthesis of [$^{18}$F] fluoropropylcarbomethoxytropane. The diluted reaction mixture is purified through HPLC using a C18 column. The labeling efficiency and radioactivity of the reaction mixture before the purification and the radioactivity of [$^{18}$F] fluoropropylcarbomethoxytropane after the purification are measured to determine the recovery of radioactivity. In addition, after the purification, high performance liquid chromatography is used to determine the radiochemical purity and the removal ratio of precursor-based organic impurities.

Example 13-2. Purification Using Silica-Based Reverse Phase Solid Phase Extraction (SPE) Cartridge The same materials and method as Example 7-2 are used, except that [$^{18}$F] fluoropropylcarbomethoxytropane is diluted with 20 mL or more of water after the preparation thereof. The diluted reaction mixture is allowed to pass through a C18 SPE cartridge so that [$^{18}$F] fluoropropylcarbomethoxytropane may be retained in the C18 SPE cartridge. To remove the residual organic solvent and polar impurities, 5 mL or more of water is used to wash the C18 SPE cartridge. Finally, [$^{18}$F] fluoropropylcarbomethoxytropane retained in the C18 SPE cartridge is eluted with 2 mL or more of ethanol to carry out purification. The labeling efficiency and radioactivity of the reaction mixture before the purification and the radioactivity of [$^{18}$F] fluoropropylcarbomethoxytropane after the purification are measured to determine the recovery of radioactivity. In addition, after the purification, high performance liquid chromatography is used to determine the radiochemical purity and the removal ratio of precursor-based organic impurities.

Example 13-3. Purification Using Polymer-Based Reverse Phase Solid Phase Extraction (SPE) Cartridge The same materials and method as Example 7-2 are used to prepare [$^{18}$F] fluoropropylcarbomethoxytropane. Then, the same materials and method as Example 13-2 are used to purify [$^{18}$F] fluoropropylcarbomethoxytropane, except that a HLB SPE cartridge is used.

The results of Example 13 are shown in the following Table 10.

TABLE 10

| | SPE cartridge | Recovery of radioactivity | Radiochemical purity | Removal ratio of precursor-based organic impurities |
|---|---|---|---|---|
| Ex. 13-1 | Silica-based reverse phase HPLC | 32.7% | 100% | 99.7% |
| Ex. 13-2 | Silica-based reverse phase SPE (C18) | 97.8% | 100 | 2.6% |
| Ex. 13-3 | Polymer-based reverse phase SPE (HLB) | 95.7% | 100 | 4.1% |

As shown in Table 10, when purification is carried out by using the silica-based reverse phase HPLC according to Example 13-1, the removal ratio of precursor-based organic impurities is significantly high. However, in this case, the recovery of radioactivity after the purification is excessively low, and the compound shows significantly low applicability as a radiopharmaceutical. Meanwhile, in the case of Examples 13-2 and 13-3, the recovery of radioactivity is significantly high but the removal ratio of precursor-based organic impurities is excessively low.

Example 14. Purification Using Silica-Based Cation Exchange SPE

Example 14-1. Purification Using Silica-Based Cation Exchange CM SPE Cartridge The same materials and method as Example 7-2 are used, except that [$^{18}$F] fluoropropylcarbomethoxytropane is diluted with 20 mL or more of water after the preparation thereof. The diluted reaction mixture is allowed to pass through a CM SPE cartridge so that [$^{18}$F] fluoropropylcarbomethoxytropane may be retained in the CM SPE cartridge. To remove the residual organic solvent and polar impurities, 5 mL or more of water is used to wash the CM SPE cartridge. Finally, [$^{18}$F] fluoropropylcarbomethoxytropane retained in the CM SPE cartridge is eluted with 2 mL or more of ethanol to carry out purification. The labeling efficiency and radioactivity of the reaction mixture before the purification and the radioactivity of [$^{18}$F] fluoropropylcarbomethoxytropane after the purification are measured to determine the recovery of radioactivity. In addition, after the purification, high performance liquid chromatography is used to determine the radiochemical purity and the removal ratio of precursor-based organic impurities.

Example 14-2. Purification Using Silica-Based Cation Exchange SCX SPE Cartridge The same materials and method as Example 14-1 are used, except that an SCX SPE cartridge is used as a cartridge for purification of [$^{18}$F] fluoropropylcarbomethoxytropane.

Example 14-3. Purification Using Silica-Based Cation Exchange WCX SPE Cartridge The same materials and method as Example 14-1 are used, except that a WCX SPE cartridge is used as a cartridge for purification of [$^{18}$F] fluoropropylcarbomethoxytropane.
The results of Example 14 are shown in the following Table 11.

Example 15. Purification Using Polymer-Based Cation Exchange SPE

Example 15-1. Purification Using Polymer-Based Cation Exchange MCX SPE Cartridge The same materials and method as Example 7-2 are used, except that [$^{18}$F] fluoropropylcarbomethoxytropane is diluted with 20 mL or more of water after the preparation thereof. The diluted reaction mixture is allowed to pass through an MCX SPE cartridge so that [$^{18}$F] fluoropropylcarbomethoxytropane may be retained in the MCX SPE cartridge. To remove the residual organic solvent and polar impurities, 5 mL or more of water is used to wash the MCX SPE cartridge. Finally, [$^{18}$F] fluoropropylcarbomethoxytropane retained in the MCX SPE cartridge is eluted with 2 mL or more of ethanol to carry out purification. The labeling efficiency and radioactivity of the reaction mixture before the purification and the radioactivity of [$^{18}$F] fluoropropylcarbomethoxytropane after the purification are measured to determine the recovery of radioactivity. In addition, after the purification, high performance liquid chromatography is used to determine the radiochemical purity and the removal ratio of precursor-based organic impurities.

Example 15-2. Purification Using Polymer-Based Cation Exchange WCX SPE Cartridge The same materials and method as Example 15-1 are used, except that a WCX SPE cartridge is used as a cartridge for purification of [$^{18}$F] fluoropropylcarbomethoxytropane.
The results of Example 15 are shown in the following Table 11.

TABLE 11

| | SPE cartridge | Recovery of radioactivity | Radiochemical purity | Removal ratio of precursor-based organic impurities |
|---|---|---|---|---|
| Ex. 14-1 | Silica-based cation exchange (CM) | 97.0% | 100 | 98.2% |
| Ex. 14-2 | Silica-based cation exchange (SCX, —SO$_3^-$) | 94.7% | 100 | 97.1% |
| Ex. 14-3 | Silica-based cation exchange (WCX, —COO$^-$) | 96.4% | 100 | 98.7% |
| Ex. 15-1 | Polymer-based cation exchange (MCX, —SO$_3^-$) | 70.2% | 100 | 96.4% |
| Ex. 15-2 | Polymer-based cation exchange (WCX, —COO$^-$) | 75.9% | 100 | 98.1% |

As shown in Table 11, when using the silica-based and polymer-based cation exchange resins are used, the removal ratio of precursor-based organic impurities is 96% or more in both cases. Thus, referring to Table 10 of Example 13, the use of a cation exchange SPE cartridge is more effective for removing precursor-based organic impurities as compared to the use of a reverse phase SPE cartridge. In addition, when purification is carried out by using a cation exchange SPE cartridge, the recovery ratio of radioactivity of silica-based SPE is 95% or more and that of polymer-based SPE is 70% or more, which demonstrates that the compounds in both cases can be used as radiopharmaceuticals.

Example 16. Purification Using Silica-Based Anion Exchange SPE

The same materials and method as Example 7-2 are used, except that [$^{18}$F] fluoropropylcarbomethoxytropane is diluted with 20 mL or more of water after the preparation thereof. The diluted reaction mixture is allowed to pass through an SAX SPE cartridge so that [$^{18}$F] fluoropropylcarbomethoxytropane may be retained in the SAX SPE cartridge. To remove the residual organic solvent and polar impurities, 5 mL or more of water is used to wash the SAX SPE cartridge. Finally, [$^{18}$F] fluoropropylcarbomethoxytropane retained in the SAX SPE cartridge is eluted with 2 mL or more of ethanol to carry out purification. The labeling efficiency and radioactivity of the reaction mixture before the purification and the radioactivity of [$^{18}$F] fluoropropylcarbomethoxytropane after the purification are measured to determine the recovery of radioactivity. In addition, after the purification, high performance liquid chromatography is used to determine the radiochemical purity and the removal ratio of precursor-based organic impurities.

The results of Example 16 are shown in the following Table 12.

Example 17. Purification Using Polymer-Based Anion Exchange SPE

Example 17-1. Purification Using Polymer-Based Anion MAX SPE Cartridge

The same materials and method as Example 7-2 are used, except that [$^{18}$F] fluoropropylcarbomethoxytropane is diluted with 20 mL or more of water after the preparation thereof. The diluted reaction mixture is allowed to pass through an MAX SPE cartridge so that [$^{18}$F] fluoropropylcarbomethoxytropane may retain in the MAX SPE cartridge. To remove the residual organic solvent and polar impurities, 5 mL or more of water is used to wash the MAX SPE cartridge. Finally, [$^{18}$F] fluoropropylcarbomethoxytropane retained in the MAX SPE cartridge is eluted with 2 mL or more of ethanol to carry out purification. The labeling efficiency and radioactivity of the reaction mixture before the purification and the radioactivity of [$^{18}$F] fluoropropylcarbomethoxytropane after the purification are measured to determine the recovery of radioactivity. In addition, after the purification, high performance liquid chromatography is used to determine the radiochemical purity and the removal ratio of precursor-based organic impurities.

Example 17-2. Purification Using Polymer-Based Anion Exchange WAX SPE Cartridge The same materials and method as Example 17-1 are used, except that a WAX SPE cartridge is used as a cartridge for purification [$^{18}$F] fluoropropylcarbomethoxytropane.

The results of Example 17 are shown in the following Table 12.

TABLE 12

| SPE cartridge | Recovery of radioactivity | Radiochemical purity | Removal ratio of precursor-based organic impurities |
|---|---|---|---|
| Ex. 16 | Silica-based anion exchange (SAX, quaternary ammonium) | 98.2% | 100 | 92.4% |
| Ex. 17-1 | Polymer-based anion exchange (MAX, quaternary ammonium) | 81.2% | 100 | 89.6% |
| Ex. 17-2 | Polymer-based anion exchange (WAX, secondary ammonium) | 70.9% | 100 | 87.0% |

As shown in Table 12, when using an anion exchange resin, a removal ratio of precursor-based organic impurities of 87% or more, which is slightly lower as compared to the cation exchange resins (see, Table 11) according to Examples 14 and 15. In addition, the recovery of radioactivity is at most 98% and at least 70%, which is similar to that of each cation exchange resin according to Examples 14 and 15.

Example 18. SPE Purification Using Both Cation and Anion Exchange

Example 18-1. SPE Purification Using Both Silica-Based Cation and Anion Exchange The same materials and method as Example 7-2 are used, except that [$^{18}$F] fluoropropylcarbomethoxytropane is diluted with 20 mL or more of water after the preparation thereof. The diluted reaction mixture is allowed to pass through SCX+SAX SPE cartridges (two cartridges connected with each other) so that [$^{18}$F] fluoropropylcarbomethoxytropane may be retained in the connected SPE cartridge. To remove the residual organic solvent and polar impurities, 5 mL or more of water is used to wash the connected SPE cartridges. Finally, [$^{18}$F] fluoropropylcarbomethoxytropane retained in the connected SPE cartridges is eluted with 2 mL or more of ethanol to carry out purification. The labeling efficiency and radioactivity of the reaction mixture before the purification and the radioactivity of [$^{18}$F] fluoropropylcarbomethoxytropane after the purification are measured to determine the recovery of radioactivity. In addition, after the purification, high performance liquid chromatography is used to determine the radiochemical purity and the removal ratio of precursor-based organic impurities.

Example 18-2. SPE Purification Using Both Polymer-Based Cation and Anion Exchange The same materials and method as Example 7-2 are used, except that [$^{18}$F] fluoropropylcarbomethoxytropane is diluted with 20 mL or more of water after the preparation thereof. The diluted reaction mixture is allowed to pass through MCX+MAX SPE cartridges (two cartridges connected with each other) so that [$^{18}$F] fluoropropylcarbomethoxytropane may be retained in the connected SPE cartridges. To remove the residual organic solvent and polar impurities, 5 mL or more of water is used to wash the connected SPE cartridges. Finally, [$^{18}$F] fluoropropylcarbomethoxytropane retained in the connected SPE cartridges is eluted with 2 mL or more of ethanol to carry out purification. The labeling efficiency and radioactivity of the reaction mixture before the purification and the radioactivity of [$^{18}$F] fluoropropylcarbomethoxytropane after the purification are measured to determine the recovery of radioactivity. In addition, after the purification, high performance liquid chromatography is used to determine the radiochemical purity and the removal ratio of precursor-based organic impurities.

The results of Example 18 are shown in the following Table 13.

TABLE 13

| SPE cartridge | Recovery of radioactivity | Radiochemical purity | Removal ratio of precursor-based organic impurities |
|---|---|---|---|
| Ex. 18-1 | Silica-based ion exchange (SCX + SAX) | 97.2% | 100 | 97.7% |

TABLE 13-continued

| SPE cartridge | Recovery of radioactivity | Radio-chemical purity | Removal ratio of precursor-based organic impurities |
|---|---|---|---|
| Ex. 18-2 Polymer-based ion exchange (MCX + MAX) | 83.1% | 100 | 98.3% |

As shown in Table 13, the types and amount of precursor-based organic impurities may vary with the conditions (base and reaction solvent) of labeling [$^{18}$F] fluoropropylcarbomethoxytropane with [$^{18}$F] fluoride. Even under the same condition, the types and amount of organic impurities may be varied due to the characteristics of a radiopharmaceutical. Therefore, it can be seen that organic impurities can be removed more stably by using a combination of a cation exchange cartridge with an anion exchange cartridge.

Example 19. Purification Using Silica-Based Ion Exchange SPE Cartridge

Example 19-1. Purification after Synthesis Using 1-Methoxy-2-Methyl-2-Propanol as Reaction Solvent To a quaternary ammonium salt support (Chromafix or QMA), [$^{18}$F] fluoride is adsorbed by passing [$^{18}$F] fluoride therethrough to carry out ion exchange and the [$^{18}$F] fluoride adsorbed to the quaternary ammonium salt support is eluted with a mixed KOMs solution having a controlled pH to a reaction container. After the elution, the eluent is removed completely by using azeotropic distillation while nitrogen gas is introduced at 100° C.

To the reaction container, 0.1 mL of acetonitrile containing (3-methanesulfonyloxypropyl)-2β-carbomryhoxy-3-β-(4-iodophenyltropane) dissolved therein as a precursor and 1.0 mL of 1-methoxy-2-methyl-2-propanol as a multifunctional reaction solvent according to the present disclosure are introduced. Then, reaction is carried out at 120° C. to obtain [$^{18}$F] fluoropropylcarbomethoxytropane.

[$^{18}$F] fluoropropylcarbomethoxytropane is diluted with 20 mL or more of water after the preparation thereof. The diluted reaction mixture is allowed to pass through SCX+ SAX SPE cartridges (two cartridges connected with each other) so that [$^{18}$F] fluoropropylcarbomethoxytropane may be retained in the connected SPE cartridges. To remove the residual organic solvent and polar impurities, 5 mL or more of water is used to wash the connected SPE cartridges. Finally, [$^{18}$F] fluoropropylcarbomethoxytropane retained in the connected SPE cartridges is eluted with 2 mL or more of ethanol and diluted with physiological saline to obtain [$^{18}$F] fluoropropylcarbomethoxytropane. Then, high performance liquid chromatography is used to determine the radiochemical purity and the removal ratio of precursor-based organic impurities.

Example 19-2. Purification after Synthesis Using Acetonitrile as Reaction Solvent The same materials and method as Example 19-1 are used to obtain [$^{18}$F] fluoropropylcarbomethoxytropane, except that 1 mL of acetonitrile is used as a reaction solvent.

Example 19-3. Purification after Synthesis Using t-Amyl Alcohol as Reaction Solvent The same materials and method as Example 19-1 are used to obtain [$^{18}$F] fluoropropylcarbomethoxytropane, except that 1 mL of t-amyl alcohol is used as a reaction solvent.

The results of Example 19 are shown in the following Table 14.

Example 20. Purification Using Polymer-Based Ion Exchange SPE Cartridge

Example 20-1. Purification after Synthesis Using 1-Methoxy-2-Methyl-2-Propanol as Reaction Solvent To a quaternary ammonium salt support (Chromafix or QMA), [$^{18}$F] fluoride is adsorbed by passing [$^{18}$F] fluoride therethrough to carry out ion exchange and the [$^{18}$F] fluoride adsorbed to the quaternary ammonium salt support is eluted with a mixed KOMs solution having a controlled pH to a reaction container. After the elution, the eluent is removed completely by using azeotropic distillation while nitrogen gas is introduced at 100° C.

To the reaction container, 0.1 mL of acetonitrile containing (3-methanesulfonyloxypropyl)-2β-carbomryhoxy-3-β-(4-iodophenyltropane) dissolved therein as a precursor and 1.0 mL of 1-methoxy-2-methyl-2-propanol as a multifunctional reaction solvent according to the present disclosure are introduced. Then, reaction is carried out at 120° C. to obtain [$^{18}$F] fluoropropylcarbomethoxytropane.

[$^{18}$F] fluoropropylcarbomethoxytropane is diluted with 20 mL or more of water after the preparation thereof. The diluted reaction mixture is allowed to pass through MCX+ MAX SPE cartridges (two cartridges connected with each other) so that [$^{18}$F] fluoropropylcarbomethoxytropane may be retained in the connected SPE cartridges. To remove the residual organic solvent and polar impurities, 5 mL or more of water is used to wash the connected SPE cartridges. Finally, [$^{18}$F] fluoropropylcarbomethoxytropane retained in the connected SPE cartridges is eluted with 2 mL or more of ethanol and diluted with physiological saline to obtain [$^{18}$F] fluoropropylcarbomethoxytropane. Then, high performance liquid chromatography is used to determine the radiochemical purity and the removal ratio of precursor-based organic impurities.

Example 20-2. Purification after Synthesis Using Acetonitrile as Reaction Solvent The same materials and method as Example 20-1 are used to obtain [$^{18}$F] fluoropropylcarbomethoxytropane, except that 1 mL of acetonitrile is used as a reaction solvent.

Example 20-3. Purification after Synthesis Using t-Amyl Alcohol as Reaction Solvent The same materials and method as Example 20-1 are used to obtain [$^{18}$F] fluoropropylcarbomethoxytropane, except that 1 mL of t-amyl alcohol is used as a reaction solvent.

The results of Example 20 are shown in the following Table 14.

Comparative Example 9. Purification Using Reverse Phase HPLC

Comparative Example 9-1. Purification after Synthesis Using 1-Methoxy-2-Methyl-2-Propanol as Reaction Solvent To a quaternary ammonium salt support (Chromafix or QMA), [$^{18}$F] fluoride is adsorbed by passing [$^{18}$F] fluoride therethrough to carry out ion exchange and the [$^{18}$F] fluoride adsorbed to the quaternary ammonium salt support is eluted with a mixed KOMs solution having a controlled pH to a reaction container. After the elution, the eluent is removed completely by using azeotropic distillation while nitrogen gas is introduced at 100° C.

To the reaction container, 0.1 mL of acetonitrile containing (3-methanesulfonyloxypropyl)-2β-carbomryhoxy-3-β-(4-iodophenyltropane) dissolved therein as a precursor and 1.0 mL of 1-methoxy-2-methyl-2-propanol as a multifunctional reaction solvent according to the present disclosure are introduced. Then, reaction is carried out at 120° C. to obtain [$^{18}$F] fluoropropylcarbomethoxytropane.

[$^{18}$F] fluoropropylcarbomethoxytropane is diluted with 8 mL of 70% methanol after the preparation thereof. The diluted reaction mixture is purified through HPLC using a C18 column. The labeling efficiency and radioactivity of the reaction mixture before the purification and the radioactivity of [$^{18}$F] fluoropropylcarbomethoxytropane after the purification are measured to determine the recovery of radioactivity. Then, [$^{18}$F] fluoropropylcarbomethoxytropane is diluted with 20 mL or more of water. The diluted reaction mixture is allowed to pass through a C18 SPE cartridge so that [$^{18}$F] fluoropropylcarbomethoxytropane may be retained in the C18 SPE cartridge. To remove the residual organic solvent and polar impurities, 5 mL or more of water is used to wash the C18 SPE cartridge. Finally, [$^{18}$F] fluoropropylcarbomethoxytropane retained in the C18 SPE cartridge is eluted with 2 mL or more of ethanol and diluted with physiological saline to obtain [$^{18}$F] fluoropropylcarbomethoxytropane. Then, high performance liquid chromatography is used to determine the radiochemical purity and the removal ratio of precursor-based organic impurities.

Comparative Example 9-2. Purification after Synthesis Using Acetonitrile as Reaction Solvent The same materials and method as Comparative Example 9-1 are used to obtain [$^{18}$F] fluoropropylcarbomethoxytropane, except that 1 mL of acetonitrile is used as a reaction solvent.

Comparative Example 9-3. Purification after Synthesis Using t-Amyl Alcohol as Reaction Solvent The same materials and method as Comparative Example 9-1 are used to obtain [$^{18}$F] fluoropropylcarbomethoxytropane, except that 1 mL of t-amyl alcohol is used as a reaction solvent.

The results of Comparative Example 9 are shown in the following Table 14.

Comparative Example 10. Purification Using Reverse Phase SPE Cartridge

Comparative Example 10-1. Purification after Synthesis Using 1-Methoxy-2-Methyl-2-Propanol as Reaction Solvent To a quaternary ammonium salt support (Chromafix or QMA), [$^{18}$F] fluoride is adsorbed by passing [$^{18}$F] fluoride therethrough to carry out ion exchange and the [$^{18}$F] fluoride adsorbed to the quaternary ammonium salt support is eluted with a mixed KOMs solution having a controlled pH to a reaction container. After the elution, the eluent is removed completely by using azeotropic distillation while nitrogen gas is introduced at 100° C.

To the reaction container, 0.1 mL of acetonitrile containing (3-methanesulfonyloxypropyl)-2β-carbomryhoxy-3-β-(4-odophenyltropane) dissolved therein as a precursor and 1.0 mL of 1-methoxy-2-methyl-2-propanol as a multifunctional reaction solvent according to the present disclosure are introduced. Then, reaction is carried out at 120° C. to obtain [$^{18}$F] fluoropropylcarbomethoxytropane.

[$^{18}$F] fluoropropylcarbomethoxytropane is diluted with 20 mL or more of water after the preparation thereof. The diluted reaction mixture is allowed to pass through a C18 SPE cartridge so that [$^{18}$F] fluoropropylcarbomethoxytropane may be retained in the C18 SPE cartridge. To remove the residual organic solvent and polar impurities, 5 mL or more of water is used to wash the C18 SPE cartridge. Finally, [$^{18}$F] fluoropropylcarbomethoxytropane retained in the C18 SPE cartridge is eluted with 2 mL or more of ethanol and diluted with physiological saline to obtain [$^{18}$F] fluoropropylcarbomethoxytropane. Then, high performance liquid chromatography is used to determine the radiochemical purity and the removal ratio of precursor-based organic impurities.

Comparative Example 10-2. Purification after Synthesis Using Acetonitrile as Reaction Solvent The same materials and method as Comparative Example 10-1 are used to obtain [$^{18}$F] fluoropropylcarbomethoxytropane, except that 1 mL of acetonitrile is used as a reaction solvent.

Comparative Example 10-3. Purification after Synthesis Using t-Amyl Alcohol as Reaction Solvent The same materials and method as Comparative Example 10-1 are used to obtain [$^{18}$F] fluoropropylcarbomethoxytropane, except that 1 mL of t-amyl alcohol is used as a reaction solvent.

The results of Comparative Example 10 are shown in the following Table 14.

TABLE 14

| | Purification method | Reaction solvent | Yield | Radiochemical purity | Removal ratio of precursor-based organic impurities |
|---|---|---|---|---|---|
| Ex. 19-1 | SCX + SAX | 1-methoxy-2-methyl-2-propanol | 62.5% | 100%% | 96.7% |
| Ex. 19-2 | | acetonitrile | 5.1% | 100% | 97.4% |
| Ex. 19-3 | | t-amyl alcohol | 7.8% | 100% | 94.6% |
| Ex. 20-1 | MCX + MAX | 1-methoxy-2-methyl-2-propanol | 70.7% | 100% | 97.8% |

TABLE 14-continued

| | Purification method | Reaction solvent | Yield | Radiochemical purity | Removal ratio of precursor-based organic impurities |
|---|---|---|---|---|---|
| Ex. 20-2 | | acetonitrile | 6.4% | 100% | 96.2% |
| Ex. 20-3 | | t-amyl alcohol | 8.6% | 100% | 96.1% |
| Comp. Ex. 9-1 | HPLC | 1-methoxy-2-methyl-2-propanol | 40.3% | 98.0% | 98.6% |
| Comp. Ex. 9-2 | | acetonitrile | 2.3% | 100% | 99.1% |
| Comp. Ex. 9-3 | | t-amyl alcohol | 8.4% | 100% | 99.4% |
| Comp. Ex. 10-1 | C18 SPE | 1-methoxy-2-methyl-2-propanol | 63.8% | 93.4% | 3.4% |
| Comp. Ex. 10-2 | | acetonitrile | 5.6% | 91.7% | 4.1% |
| Comp. Ex. 10-3 | | t-amyl alcohol | 3.7% | 94.1% | 3.7% |

As shown in Table 14, when purifying [$^{18}$F] fluoropropylcarbomethoxytropane by using HPLC, the highest removal ratio of organic impurities is provided. However, in the case of purification using HPLC, the start point and end point of separation are determined by the workers and the results may depend on the number of use of a HPLC column or preparation accuracy of a mobile phase. In other words, HPLC may provide a different result depending on the skill of a worker. However, in the case of SPE purification, there is no place of intervention of the worker since SPE is carried out integrally by the system. Thus, SPE purification is not affected by the skill of a worker and always provides constant results advantageously, and thus is more suitable for the preparation of a radiopharmaceutical. Meanwhile, in the case of a currently used reverse phase C18 SPE, it is possible to obtain high yield and radiochemical purity. However, such reverse phase C18 SPE shows a significantly lower removal ratio of precursor-based organic impurities as compared to ion exchange SPE purification. Thus, it is difficult to apply reverse phase C18 SPE to [$^{18}$F] fluoropropylcarbomethoxytropane requiring a high specific radioactivity (mCi/μmol). On the contrary, when using cation and anion exchange SPE cartridges, it is possible to remove most of ionic organic impurities. Thus, it is possible to remove most precursor-based organic impurities.

Hereinafter, the method for preparing a radiopharmaceutical by using a cassette including a backflow-preventing reaction container according to an embodiment will be explained in more detail.

FIG. 1 is a schematic view illustrating a process for preparing a radiopharmaceutical by using a cassette including a backflow-preventing reaction container according to an embodiment.

The backflow-preventing reaction container 10 according to an embodiment includes a first line 11 through which the reagents used for the synthesis of a radiopharmaceutical is supplied and a second line 13 for providing the inner part of the reaction container 10 with a vacuum state. The first line 11 is connected to the inlets for supplying each of the reagents, including a solution providing [$^{18}$F] fluoride, a precursor for radiopharmaceutical and a reaction solvent for use in labeling of the precursor with [$^{18}$F] fluoride, and an inlet for nitrogen or air in the form of a manifold, thereby forming a cassette. Therefore, the cassette may include a single manifold or a plurality of manifolds. The cassette for a radiopharmaceutical may include other known constitutional parts as long as the reaction container for radiopharmaceutical is the backflow-preventing reaction container according to the present disclosure.

The end point E of the first line 11 is positioned at a height spaced apart from the bottom surface of the backflow-preventing reaction container 10. Preferably, the end point E of the first line 11 is positioned at a height h spaced from the surface of the materials supplied to the backflow-preventing reaction container 10 by a predetermined interval. More preferably, the interval between the end point E of the first line 11 and the surface of the whole reagents supplied to the backflow-preventing reaction container 10 for the synthesis of a radiopharmaceutical is at most 5 cm. In other words, the end point E of the first line 11 may be positioned at a height at least 0 cm and at most 5 cm higher than the surface of the whole reagents supplied to the backflow-preventing reaction container 10 for the synthesis of a radiopharmaceutical.

Referring to FIG. 1, the end point E of the first line 11 is positioned at height spaced apart from the bottom surface of the backflow-preventing reaction container 10 by a predetermined interval and F-18 solution 20 is supplied through the first line 11 ((A) in FIG. 1). Since the end point E of the first line 11 is positioned at a height higher than the bottom surface of the backflow-preventing reaction container 10 by a predetermined interval, F-18 solution 20 is supplied stably without splattering ((B) in FIG. 1) so that the solution may be supplied stably to the bottom of the backflow-preventing reaction container 10 ((C) in FIG. 1). Even when nitrogen or air is supplied through the first line 11 to dry the F-18 solution supplied to the reaction container ((D) in FIG. 1), the F-18 solution 20 does not form bubbles due to the nitrogen or air since the end point E of the first line 11 is positioned at a height higher than the bottom surface of the backflow-preventing reaction container 10 by a predetermined interval. Thus, it is possible to prevent the F-18 solution from splattering to the walls of the backflow-preventing reaction container 10 ((E) in FIG. 1). After the F-18 solution 20 is dried, a precursor 30 of radiopharmaceutical is supplied through the first line 11. Similarly, the precursor 30 of radiopharmaceutical is supplied stably onto the F-18 solution 20 without splattering ((F) and (G) in FIG. 1). Then, a reaction solvent 40 is supplied through the first line 11 to carry out reaction of labeling of the precursor of radiopharmaceutical with F-18. In this case, the end point E of the first line 11 is positioned at a height higher than the surface of the whole reagents supplied to the backflow-preventing reaction container 10 by a predetermined interval, and thus the reaction solvent 40 does not undergo backflow to the first line 11 even when the temperature is increased to 100-140° C. for the labeling reaction. Therefore, most of the reaction solvent can participate in the labeling reaction in the backflow-preventing reaction container 10 in an amount as much as the supply thereof. As a result, it is possible to prepare a radiopharmaceutical stably, and to provide improved yield of radiopharmaceutical. In addition, since no reaction solvent 40 undergoes backflow to the first line 11, the reaction solvent 40 does not backflow to a cassette to which the other stage of the first line 11 having no end point E is connected, thereby preventing the cassette from being damaged.

Figure 2:
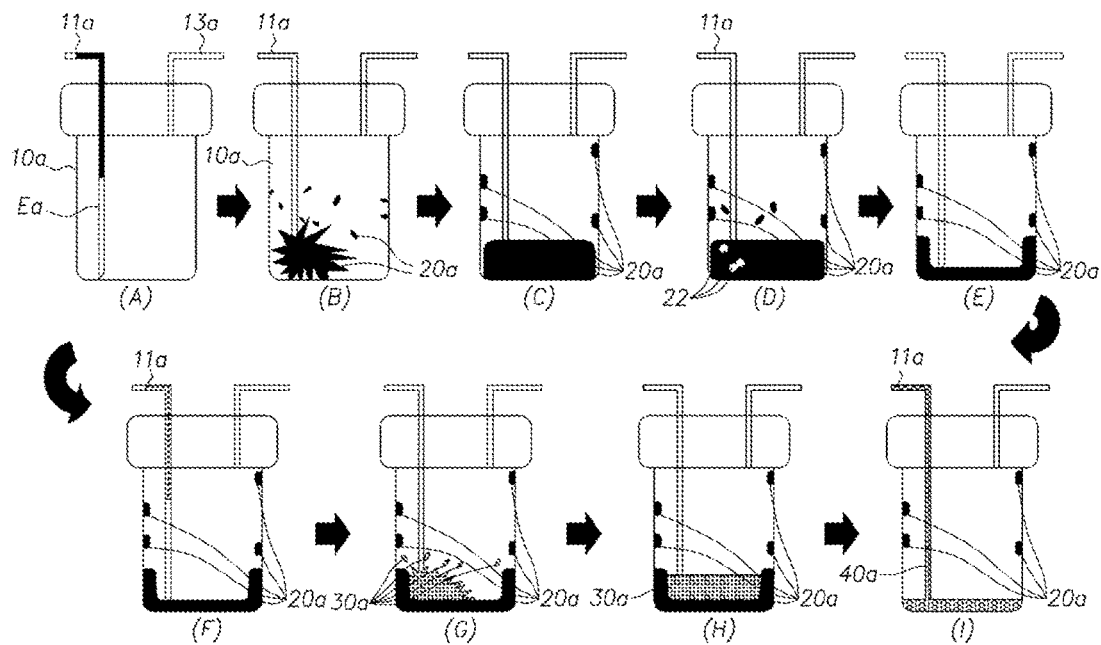
FIG. 2 is a schematic view illustrating a process for preparing a radiopharmaceutical by using a cassette including a conventional reaction container.

As compared to the present disclosure, a method for preparing a radiopharmaceutical by using a cassette including a conventional reaction container will be discussed with reference to FIG. 1. FIG. 2 is a schematic view illustrating a process for preparing a radiopharmaceutical by using a cassette including a conventional reaction container. Referring to FIG. 2, the end point Ea of a reagent-supplying line 11*a* for supplying and recovering reagents is provided in such a manner that it reaches to the bottom surface of a reaction container 10*a* in order to increase the recovery ratio ((A) in FIG. 2). Therefore, when F-18 solution 20*a* is supplied through the reagent-supplying line 11*a*, F-18 solution splatters to the walls of the reaction container 10*a* ((B) in FIG. 2) and a certain amount of F-18 solution 20*a* is applied to the walls of the reaction container 10*a* ((C) in FIG. 2). In addition, when nitrogen or air is supplied through the reagent-supplying line 11*a* to dry the F-18 solution 20*a*, nitrogen or air is supplied to the F-18 solution 20*a* to generate air bubbles ((D) in FIG. 2). For this, a larger amount of F-18 solution splatters to the walls of the reaction container 10*a* ((E) in FIG. 2). Then, a precursor of radiopharmaceutical is supplied to the reagent-supplying line 11*a* ((F) in FIG. 2) and it also splatters to the walls of the reaction container 10*a* like the F-18 solution 20*a* ((G) in FIG. 2). Thus, a certain amount of precursor of radiopharmaceutical also remains on the walls in the form of drops ((H) in FIG. 2). This is because the reagent-supplying line 11*a* is in contact with the bottom surface of the reaction container 10*a*. After that, a reaction solvent 40*a* is injected through the reagent-supplying line 11*a* to carry out labeling of the precursor of radiopharmaceutical with F-18. Such labeling is carried out generally at 100-140° C., which exceeds the boiling point of the reaction solvent 40*a*. As a result, the reaction solvent 40*a* is vaporized to apply a positive pressure, which causes backflow of the reaction solvent 40*a* to the reagent-supplying line 11*a* so that a certain amount of the reaction solvent 40*a* cannot participate in the labeling ((I) in FIG. 2). Therefore, the other stage of the reagent-supplying line 11*a* having no end point Ea is connected to a cassette and the cassette may be damaged during the above process, when the cassette is not resistant against the reaction solvent 40*a* depending on the particular type thereof. In this case, it is not possible to recover the reaction materials, resulting in a failure in preparation of a radiopharmaceutical.

Therefore, when a radiopharmaceutical is prepared by using a cassette including the backflow-preventing reaction container 10 according to the present disclosure, the reaction solvent causes no backflow to the first line 11 and a problem of damages upon the cassette caused by such backflow is solved. In addition, there is no need for developing a material for a cassette resistant against the reaction solvent, thereby reducing the cost. Thus, most of the reaction solvent 40 supplied to the reaction container can participate in the labeling reaction, thereby improving the yield of a radiopharmaceutical. Further, it is possible to allow preparation of a radiopharmaceutical suitable for good manufacturing practice (GMP).

Referring to FIG. 1, the reaction solvent used for the method for preparing a radiopharmaceutical by using a cassette including a backflow-preventing reaction container 10 according to the present disclosure may include any one selected from aprotic solvents, protic solvents and multifunctional solvents.

The aprotic solvent may include any one selected from acetonitrile, dimethyl formamide and dimethyl sulfoxide The protic solvent may include any one selected from the group consisting of primary alcohols including methanol, ethanol, n-propanol, n-butanol, n-amyl alcohol, n-hexyl alcohol, n-heptanol and n-octanol, secondary alcohols including isopropanol, isobutanol, isoamyl alcohol and 3-pentanol, and tertiary alcohols including t-butanol, t-amyl alcohol, 2,3-dimethyl-2-butanol, 2-(trifluoromethyl)-2-propanol, 3-methyl-3-pentaol, 3-ethyl-3-pentanol, 2-methyl-2-pentaol, 2,3-dimethyl-3-pentanol, 2,4-dimethyl-2-pentanol, 2-methyl-2-hexanol, 2-cyclopropyl-2-propanol, 2-cyclopropyl-2-butanol, 2-cyclopropyl-3-methyl-2-butanol, 1-methyl-cyclopentaol, 1-ethylcyclonentaol, 1-propylcyclopentaol, 1-methylcyclohexanol, 1-ethylcyclohexanol and 1-methyl-cycloheptanol.

The multifunctional solvent is a compound represented by Chemical Formula 1:

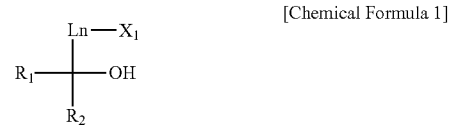

[Chemical Formula 1]

wherein each of $R_1$ and $R_2$ independently represents H, a C1-C10 alkyl group or the same functional group as $X_1$;

Ln represents a C1-C10 alkyl group or is a polyethylene glycol represented by $CH_2(OCH_2CH_2)_n$ wherein n is an integer of 1-10;

$X_1$ represents any one polar group selected from an alkoxy group ($OR_3$), nitrile group (CN) and halide, and $R_3$ preferably represents a C1-C10 alkyl group).

Herein, Ln preferably represents a C1-C3 alkyl group or is a polyethylene glycol represented by $CH_2(OCH_2CH_2)_n$ wherein n is an integer of 1-3.

Preferably, the alkoxy group is any one selected from methoxy, ethoxy, propoxy, isopropoxy and t-butoxy.

Preferably, the halide is any one selected from chloride (Cl), bromide (Br) and iodide (I).

Preferably, each of $R_1$ and $R_2$ represents methyl or ethyl.

Preferably, the multifunctional solvent represented by Chemical Formula 1 is any one selected from the group consisting of 1-methoxy-2-methyl-2-propanol, 1-ethoxy-2-methyl-2-propanol, 1-propoxy-2-methyl-2-propanol, 1-isopropoxy-2-methyl-2-propanol, 1-t-butoxy-2-methyl-2-propanol, 1-nitrile-2-methyl-2-propanol, 1-chloro-2-metyl-2-propanol, 1-bromo-2-methyl-2-propanol, 1-iodo-2-methyl-2-propanol, 1-(2-methoxyethoxy)-2-methyl-2-propanol and 3-(methoxymethyl)-3-pentanol.

Therefore, the method for preparing a radiopharmaceutical by using a cassette including a backflow-preventing reaction container 10 according to an embodiment includes the steps of: eluting [$^{18}$F] fluoride through the backflow-preventing reaction container 10 ((A) to (C) in FIG. 1); drying the eluent in the backflow-preventing reaction container ((D) and (E) in FIG. 1); and supplying a precursor of a radiopharmaceutical and a reaction solvent into the backflow-preventing reaction container so that the dried [$^{18}$F] fluoride may react with the precursor of a radiopharmaceutical in the presence of the reaction solvent ((F) to (H) in FIG. 1). For example, the elution step is carried out by allowing [$^{18}$F] fluoride to pass through a quaternary ammonium salt support (Chromafix or QMA) to carry out anion exchange so that quaternary ammonium support may be absorbed, and eluting the [$^{18}$F] fluoride adsorbed on the quaternary ammonium salt support to the backflow-preventing reaction container 10 with a mixed KOMs solution having a controlled pH. The drying step is carried out by drying the eluent with nitrogen or air through the first line 11 at a predetermined temperature, such as 100-140° C. The reaction step is carried out by introducing the precursor of a radiopharmaceutical and reaction solvent through the first line 11 to carry out reaction at 100-140° C. and to obtain a radiopharmaceutical labeled with F-18. After the synthesis, the method may further include a purification step using a solid phase extraction (SPE) process or HPLC purification process. In the case of such a solid phase extraction (SPE) or HPLC process, the methods according to any one of Examples 12-19 may be used. In addition, the elution step, drying step, synthesis step and purification step may be carried out by using methods generally used for the preparation of a radiopharmaceutical.

The method for preparing a radiopharmaceutical by using a cassette including a backflow-preventing reaction container 10 according to the present disclosure may be used for preparing any types of organic compounds labeled with F-18.

Thus, the fluorine salt as a source of F-18 fluoride used herein preferably includes a compound containing fluorine-18 and may be selected from: alkali metal fluorides including an alkali metal selected from the group consisting of lithium, sodium, potassium, rubidium and cesium; alkaline earth metal fluorides including an alkaline earth metal selected from the group consisting of magnesium, calcium, strontium and barium; and ammonium fluorides. However, the fluorine salt may be potassium fluoride or an ammonium fluoride, more preferably. Preferably, the potassium-containing alkali metal fluoride or tetraalkylammonium fluoride may be adsorbed on any one support selected from Celite, molecular sieves, alumina and silica gel. Preferably, the ammonium fluoride may be selected from the group consisting of: quaternary ammonium fluorides including tetrabutylammonium fluoride and benzyltrimethylammonium fluoride; tertiary ammonium fluorides including triethylammonium fluoride and tributylammonium fluoride; secondary ammonium fluorides including dibutylammonium fluoride and dihexylammonium fluoride; and primary ammonium fluoride including butylammonium fluoride and hexylammonium fluoride. More preferably, the ammonium fluoride may be tetrabutylammonium fluoride. The fluorine salt may be used in an amount of 1 pg-100 ng of [$^{18}$F] fluoride per milligram of the precursor of a radiopharmaceutical described hereinafter.

In addition, the precursor of a radiopharmaceutical used herein may be an alkyl halide or alkyl sulfonate, preferably. In the alkyl halide or alkyl sulfonate, the halide is selected from Cl, Br and I, except F, and the sulfonate is —SO$_3$R$^{12}$, wherein R$_{12}$ is an alkyl or aryl group. More particularly, the alkyl group is a C1-C12 alkyl sulfonate or haloC1-C12 alkyl group and a particular example thereof is selected from the group consisting of methanesulfonate, ethanesulfonate, isopropanesulfonate, chloromethanesulfonate, trifluorometh-anesulfonate and chloroethanesulfonate. In addition, the aryl group is preferably selected from a phenyl, C1-C4 alkylphenyl, halophenyl, C1-C4 alkoxyphenyl and nitrophenyl, and a preferred example thereof is methylphenyl sulfonate, ethylphenyl sulfonate, chlorophenyl sulfonate, bromophenyl sulfonate, methoxyphenyl sulfonate or nitrophenylsulfonyl. In addition, the precursor of a radiopharmaceutical used herein may also include an aliphatic compound having a leaving group used for the methods for preparing an organic fluorinated aliphatic compound in Examples 1-11.

For example, the radiopharmaceutical that may be obtained from the method for preparing a radiopharmaceutical by using a cassette including a reaction container 10 according to the present disclosure may include at least one selected from the group consisting of the following radiopharmaceuticals:

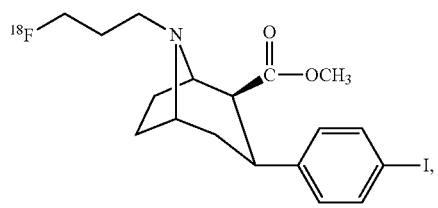

[$^{18}$F] fluoropropylcarbomethoxytropane

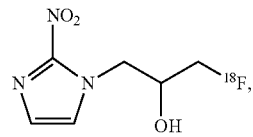

[18F] fluoromisonidazole

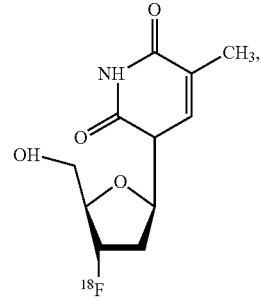

[18F] fluorothymidine

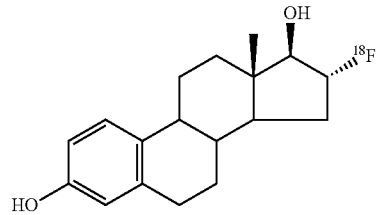

[18F] fluoroestradiol

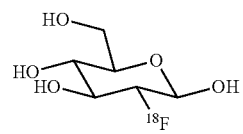

[18F] fluorodeoxyglucose

Hereinafter, the present disclosure will be explained in more detail with reference to the following examples. The following examples are for illustrative purposes only and not intended to limit the scope of the present disclosure. It will be understood by those skilled in the art that various changes in form and details may be made thereto without departing from the scope of this disclosure as defined by the appended claims. Therefore, it is intended that the scope of the present disclosure includes all embodiments falling within the spirit and scope of the appended claims.

Examples 21 and 22. Preparation of [$^{18}$F] Fluoropropylcarbomethoxytropane

The backflow-preventing reaction container 10 as shown in FIG. 1 is applied to TRACERlab MXFDG Cassette (GE healthcare) and TRACERlab MX is used as an automatic synthesis system to obtain [$^{18}$F] fluoropropylcarbomethoxytropane.

First, 0.1 mL of acetonitrile in which 4 mg of (3-methansulfonyloxypropyl)-2β-carbomethoxy-3-β-(4-iodophenyl)tropane or (3-toluenesulfonyloxypropyl)-2β-carbomethoxy-3-β-(4-iodophenyl)tropane is dissolved and 1.0 mL of 1-methoxy-2-methyl-2-propanol as a multifunctional reaction solvent are introduced. Then, reaction is carried out at 120° C. for 10-20 minutes to obtain [$^{18}$F] fluoropropylcarbomethoxytropane.

Examples 23 and 24. Preparation of [$^{18}$F] Fluoropropylcarbomethoxytropane

The backflow-preventing reaction container 10 as shown in FIG. 1 is applied to TRACERlab MXFDG Cassette (GE healthcare) and TRACERlab MX is used as an automatic synthesis system to obtain [$^{18}$F] fluoropropylcarbomethoxytropane.

First, 0.1 mL of acetonitrile in which 4 mg of (3-methansulfonyloxypropyl)-2β-carbomethoxy-3β-(4-iodophenyl)tropane or (3-toluenesulfonyloxypropyl)-2β-carbomethoxy-3-β(4-iodophenyl)tropane is dissolved and 1.0 mL of t-amyl alcohol as a protic solvent are introduced. Then, reaction is carried out at 120° C. for 10-20 minutes to obtain [$^{18}$F] fluoropropylcarbomethoxytropane.

Examples 25 and 26. Preparation of [$^{18}$F] Fluoropropylcarbomethoxytropane

The backflow-preventing reaction container 10 as shown in FIG. 1 is applied to TRACERlab MXFDG Cassette (GE healthcare) and TRACERlab MX is used as an automatic synthesis system to obtain [$^{18}$F] fluoropropylcarbomethoxytropane.

First, 1.1 mL of acetonitrile in which 4 mg of (3-methansulfonyloxipropyl)-2β-carbomethoxy-3β-(4-iodophenyl)tropane or (3-toluenesulfonyloxipropyl)-2β-carbomethoxy-3-β-(4-iodophenyl)tropane is dissolved is introduced. Then, reaction is carried out at 120° C. for 10-20 minutes to obtain [$^{18}$F] fluoropropylcarbomethoxytropane.

Comparative Examples 11-16. Preparation of [$^{18}$F] Fluoropropylcarbomethoxytropane The conventional TRACERlab MXFDG Cassette (GE healthcare) including the reaction container 10*a* as shown in FIG. 2 and TRACERlab MX as an automatic synthesis system are used to obtain [$^{18}$F] fluoropropylcarbomethoxytropane by using the same reagents under the same conditions as Examples 21-26.

The following Table 15 shows the results including the yield of radiopharmaceutical according to each of Examples 21-26 and Comparative Examples 11-16 and whether each cassette is damaged or not.

TABLE 15

| | Reaction container | Precursor | Reaction solvent | Yield |
|---|---|---|---|---|
| Ex. 21 | Backflow-preventing reaction container | FP-CIT-OMs | 1-methoxy-2-methyl-2-propanol | 31.21% |
| Ex. 22 | | FP-CIT-OTs | 1-methoxy-2-methyl-2-propanol | 32.94% |
| Ex. 23 | | FP-CIT-OMs | t-amyl alcohol | 20.12% |
| Ex. 24 | | FP-CIT-OTs | t-amyl alcohol | 23.07% |
| Ex. 25 | | FP-CIT-OMs | acetonitrile | 10.61% |
| Ex. 26 | | FP-CIT-OTs | acetonitrile | 11.04% |
| Comp. Ex. 11 | Conventional reaction container | FP-CIT-OMs | 1-methoxy-2-methyl-2-propanol | 0% (cassette damaged) |
| Comp. Ex. 12 | | FP-CIT-OTs | 1-methoxy-2-methyl-2-propanol | 0% (cassette damaged) |
| Comp. Ex. 13 | | FP-CIT-OMs | t-amyl alcohol | 0% (cassette damaged) |
| Comp. Ex. 14 | | FP-CIT-OTs | t-amyl alcohol | 0% (cassette damaged) |
| Comp. Ex. 15 | | FP-CIT-OMs | acetonitrile | 1.41% |
| Comp. Ex. 16 | | FP-CIT-OTs | acetonitrile | 2.19% |

As shown in Table 15, when a radiopharmaceutical is prepared by using the backflow-preventing reaction container according to the present disclosure (Examples 21-26), it is possible to obtain a radiopharmaceutical stably with high yield without damages on the cassette. Particularly, even when using acetonitrile (Examples 25 and 26), it is possible to obtain a radiopharmaceutical with a yield of about 10%. In the case of t-amyl alcohol (Examples 23 and 24), FP-CIT is prepared with a yield of 20-23%. In the case of 1-methoxy-2-methyl-2-propanol (Examples 21 and 22), it is possible to obtain a high yield of 31-33% increased by about 10% due to a decrease in production time.

On the other hand, when a radiopharmaceutical is prepared by using the conventional reaction container as it is (Comparative Examples 11-16), a general cassette not resistant against 1-methoxy-2-methyl-2-propanol and t-amyl alcohol is damaged due to the backflow of the reaction solvent during the reaction, resulting in a failure in preparation of a radiopharmaceutical. Even when using acetonitrile applicable to the cassette as a reaction solvent, the yield is as low as about 1-2% since the reagents cannot totally participate in the reaction, and thus the conventional reaction container cannot be applied practically.

Example 27. Preparation of [$^{18}$F] Fluorothymidine

The backflow-preventing reaction container 10 as shown in FIG. 1 is applied to TRACERlab MXFDG Cassette (GE healthcare) and TRACERlab MX is used as an automatic synthesis system to obtain [$^{18}$F] fluorothymidine.

First, 1.1 mL of acetonitrile in which 5 mg of 5'-O-DMTr-2'-deoxy-3'-O-nosyl-b-D-threo-pentofuranosyl)-3-N-BOC-thymine is dissolved is introduced. Then, reaction is carried out at 120° C. for 10-20 minutes to obtain [$^{18}$F] fluorothymidine.

Comparative Examples 17. Preparation of [$^{18}$F] Fluorothymidine

The conventional TRACERlab MXFDG Cassette (GE healthcare) including the reaction container 10*a* as shown in FIG. 2 and TRACERlab MX as an automatic synthesis system are used to obtain [$^{18}$F] fluorothymidine by using the same reagents under the same conditions as Example 27.

Example 28. Preparation of [$^{18}$F] Fluoromisonidazole

The backflow-preventing reaction container 10 as shown in FIG. 1 is applied to TRACERlab MXFDG Cassette (GE healthcare) and TRACERlab MX is used as an automatic synthesis system to obtain [$^{18}$F] fluoromisonidazole.

First, 1.1 mL of acetonitrile in which 1-2 mg of 3-(2-nitroimidazol-1-yl)-2-O-tetrahydropyranyl-1-O-toluenesulfonyl propanediol is dissolved is introduced. Then, reaction is carried out at 100° C. for 10-20 minutes to obtain [$^{18}$F] fluoromisonidazole.

Comparative Examples 18. Preparation of [$^{18}$F] Fluoromisonidazole

The conventional TRACERlab MXFDG Cassette (GE healthcare) including the reaction container 10*a* as shown in FIG. 2 and TRACERlab MX as an automatic synthesis system are used to obtain [$^{18}$F] fluoromisonidazole by using the same reagents under the same conditions as Example 28.

Example 29. Preparation of [$^{18}$F] Fluoroestradiol

The backflow-preventing reaction container 10 as shown in FIG. 1 is applied to TRACERlab MXFDG Cassette (GE healthcare) and TRACERlab MX is used as an automatic synthesis system to obtain [$^{18}$F] fluoroestradiol.

First, 1.1 mL of acetonitrile in which 0.5-1 mg of 3-(Methoxymethoxy)-1,3,5(10)-gonatriene-16beta, 17beta diol-16,17-cyclic sulfate is dissolved is introduced. Then, reaction is carried out at 100° C. for 10-20 minutes to obtain [$^{18}$F] fluoroestradiol.

Comparative Examples 19. Preparation of [$^{18}$F] Fluoroestradiol

The conventional TRACERlab MXFDG Cassette (GE healthcare) including the reaction container 10*a* as shown in FIG. 2 and TRACERlab MX as an automatic synthesis system are used to obtain [$^{18}$F] fluoroestradiol by using the same reagents under the same conditions as Example 29.

The following Table 16 shows the yield of a radiopharmaceutical according to each of Examples 27-29 and Comparative Examples 17-19.

TABLE 16

| | Reaction container | Radiopharmaceutical | Yield |
|---|---|---|---|
| Ex. 27 | Backflow-preventing reaction container | FLT | 25.08% |
| Ex. 28 | | FMISO | 25.13% |
| Ex. 29 | | FES | 30.62% |

TABLE 16-continued

| | Reaction container | Radiopharmaceutical | Yield |
|---|---|---|---|
| Comp. Ex. 17 | Conventional reaction container | FLT | 3.72% |
| Comp. Ex. 18 | | FMISO | 5.14% |
| Comp. Ex. 19 | | FES | 1.41% |

As shown in Table 16, when using a precursor in a small amount of 0.5-5 mg like Comparative Examples 17-19, the reagents cannot participate in the reaction, resulting in a significantly low yield of about 1-3%. However, in the case of Examples 27-29, the whole reagents can participate in the reaction, resulting in an increase in yield of a radiopharmaceutical by at least 5 times to at most 30 times of the yield according to Comparative Examples 17-19.

While the present disclosure has been described with respect to the specific embodiments, it will be apparent to those skilled in the art that various changes and modifications may be made without departing from the spirit and scope of the disclosure as defined in the following claims and equivalents thereof.

The invention claimed is:

1. A method for preparing an aliphatic compound labeled with $^{18}F$, the method comprising:
reacting a fluorine salt having $^{18}F$ with an aliphatic compound containing a leaving group in a multifunctional solvent represented by the following Chemical Formula 1 to substitute the leaving group of the aliphatic compound with the $^{18}F$ of the fluorine salt, thereby obtaining the aliphatic compound labeled with [$^{18}F$]:

[Chemical Formula 1]

wherein each of $R_1$ and $R_2$ independently represents H, a C1-C10 alkyl group or the same functional group as $X_1$;
Ln represents a C1-C10 alkyl group or is a polyethylene glycol represented by $CH_2(OCH_2CH_2)_n$ wherein n is an integer of 1 to 10;
$X_1$ represents an alkoxy group ($OR_3$); and
$R_3$ represents a C1-C10 alkyl group.

2. The method of claim 1, wherein Ln is a C1-C3 alkyl group or polyethylene glycol represented by $CH_2(OCH_2CH_2)_n$ in which n is an integer of 1 to 3.

3. The method of claim 1, wherein the alkoxy group ($OR_3$) is selected from the group consisting of methoxy, ethoxy, propoxy, isopropoxy and t-butoxy.

4. The method of claim 1, wherein each of $R_1$ and $R_2$ is a methyl group or an ethyl group.

5. The method of claim 1, wherein the multifunctional solvent represented by Chemical Formula 1 is selected from the group consisting of 1-methoxy-2-methyl-2-propanol, 1-ethoxy-2-methyl-2-propanol, 1-propoxy-2-methyl-2-propanol, 1-isopropoxy-2-methyl-2-propanol, 1-t-butoxy-2-methyl-2-propanol, 1-nitrile-2-methyl-2-propanol, 1-chloro-2-methyl-2-propanol, 1-bromo-2-methyl-2-propanol, 1-iodo-2-methyl-2-propanol, 1-(2-methoxyethoxy)-2-methyl-2-propanol, and 3-(methoxymethyl)-3-pentanol.

6. The method of claim 1, wherein the leaving group-containing aliphatic compound has an alkyl halide group or alkyl sulfonate group, and the halide group or the sulfonate group is the leaving group.

7. The method of claim 1, wherein the leaving group-containing aliphatic compound is a compound having an alkyl halide group or an alkyl sulfonate group, and the halide group or the sulfonate group is a primary leaving group or a secondary leaving group.

8. The method of claim 1, wherein the leaving group-containing aliphatic compound contains N—$(CH_2)n$-$X_2$ or O—$(CH_2)n$-$X_2$, wherein $X_2$ is the leaving group and n is an integer of 1 to 10.

9. The method of claim 8, wherein $X_2$ is a halide group or sulfonate group.

10. The method of claim 6, wherein the halide group is selected from the group consisting of Cl, Br and I.

11. The method of claim 6, wherein the sulfonate group is —$SO_3R_{12}$ wherein $R_{12}$ is selected from the group consisting of a C1-C12 alkyl, halo C1-C12 alkyl, phenyl, C1-C4 alkylphenyl, halophenyl, C1-C4 alkoxy, and nitrophenyl.

12. The method of claim 1, further comprising purifying the [$^{18}F$]-labeled aliphatic compound by using at least one ion exchange solid phase extraction (SPE) cartridge.

13. The method of claim 12, wherein the ion exchange SPE cartridge is selected from the group consisting of a cation exchange SPE cartridge, an anion exchange SPE cartridge, and a combination thereof.

14. The method of claim 13, wherein the ion exchange SPE cartridge comprises a solid support including either a polymer containing a phenyl group and C1-C20 hydrocarbon, or silica.

15. The method of claim 14, wherein the ion exchange SPE cartridge comprises the cation exchange SPE cartridge selected from the group consisting of a silica-based strong cation exchange (SCX) SPE cartridge, a polymer-based mixed-mode strong cation exchange (MCX) SPE cartridge, a polymer-based weak cation exchange (WCX) SPE cartridge, and a combination thereof.

16. The method of claim 14, wherein the ion exchange SPE cartridge comprises the anion exchange SPE cartridge selected from the group consisting of a silica-based strong anion exchange (SAX) SPE cartridge, a polymer-based mixed-mode strong anion exchange (MAX) SPE cartridge, a polymer-based weak cation exchange (WAX) SPE cartridge, and a combination thereof.

17. The method of claim 1 further comprising:
after the reacting, purifying the aliphatic compound labeled with $^{18}F$ through solid phase extraction (SPE) carried out by using an ion exchange SPE cartridge comprising a first ion exchange SPE cartridge represented by the following Chemical Formula 2:

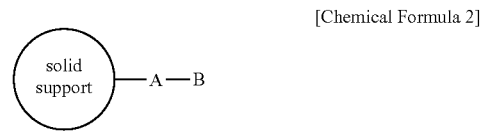

[Chemical Formula 2]

wherein the solid support is either a polymer containing a phenyl group and C1-C20 hydrocarbon, or silica;
A is null when the solid support is the polymer, or a phenyl or a Cl 1-C20 hydrocarbon group when the solid support is the silica; and
B is an organic anion.

18. The method of claim 17, wherein the ion exchange SPE cartridge comprises:
the first ion exchange SPE cartridge; and
a second ion exchange cartridge of Chemical Formula 2,

[Chemical Formula 2]

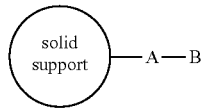

wherein the solid support is either a polymer containing a phenyl group and C1-C20 hydrocarbon, or silica;
A is null when the solid support is the polymer, or a phenyl or a C1-C20 hydrocarbon group when the solid support is the silica;
B is an organic cation selected from the group consisting of:
(i)

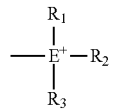

wherein E is nitrogen or phosphorus and $R_1$, $R_2$ and $R_3$ are the same or different from one another, and each represents C1-C20 hydrocarbon group;
(ii)

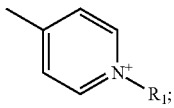

and
(iii) a C2-C20 heteroaromatic cation having at least two nitrogen atoms, nitrogen and oxygen, or nitrogen and sulfur and having a substituent of a C1-20 hydrocarbon group at the position of one nitrogen atom, and
the organic anion is sulfonic acid (—$SO^{3-}$) or carboxylic acid (—$COO^-$).

19. The method of claim 1, further comprising:
after the reacting, purifying the aliphatic compound labeled with $^{18}F$ through solid phase extraction (SPE) carried out by using at least one ion exchange SPE cartridge, wherein the organic fluorinated aliphatic compound is [$^{18}F$] fluoropropyl carbomethoxytropane.

20. The method of claim 19, wherein the ion exchange SPE cartridge is selected from the group consisting of a cation exchange SPE cartridge, an anion exchange SPE cartridge, and a combination thereof.

21. The method of claim 20, wherein the ion exchange SPE cartridge comprises a solid support including either a polymer containing a phenyl group and C1-C20 hydrocarbon, or silica.

22. The method of claim 21, wherein the ion exchange SPE cartridge comprises the cation exchange SPE cartridge selected from the group consisting of a silica-based strong cation exchange (SCX) SPE cartridge, a polymer-based strong cation exchange (MCX) SPE cartridge, a polymer-based weak cation exchange (WCX) SPE cartridge, and a combination thereof.

23. The method of claim 21, wherein the ion exchange SPE cartridge comprises the anion exchange SPE cartridge selected from the group consisting of a silica-based strong anion exchange (SAX) SPE cartridge, a polymer-based mixed-mode strong anion exchange (MAX) SPE cartridge, a polymer-based weak anion exchange (WAX) SPE cartridge, and a combination thereof.

* * * * *